(12) United States Patent
Eveleth et al.

(10) Patent No.: US 11,103,553 B2
(45) Date of Patent: Aug. 31, 2021

(54) MODIFIED FIBROBLAST GROWTH FACTORS FOR THE TREATMENT OF OCULAR DISORDERS

(71) Applicant: TREFOIL THERAPEUTICS, INC., San Diego, CA (US)

(72) Inventors: David Eveleth, San Diego, CA (US); Kenneth A. Thomas, Jr., Chatham, NJ (US)

(73) Assignee: TREFOIL THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/024,824

(22) PCT Filed: Sep. 24, 2014

(86) PCT No.: PCT/US2014/057302
§ 371 (c)(1),
(2) Date: Mar. 24, 2016

(87) PCT Pub. No.: WO2015/048188
PCT Pub. Date: Apr. 2, 2015

(65) Prior Publication Data
US 2016/0263190 A1 Sep. 15, 2016

Related U.S. Application Data

(60) Provisional application No. 61/882,561, filed on Sep. 25, 2013.

(51) Int. Cl.
*A61K 38/18* (2006.01)
*C07K 14/50* (2006.01)
*A61K 9/00* (2006.01)

(52) U.S. Cl.
CPC ........ *A61K 38/1825* (2013.01); *A61K 9/0048* (2013.01); *C07K 14/501* (2013.01)

(58) Field of Classification Search
None
See application file for complete search history.

(56) References Cited

U.S. PATENT DOCUMENTS

| | | | |
|---|---|---|---|
| 5,033,252 A | 7/1991 | Carter | |
| 5,052,558 A | 10/1991 | Carter | |
| 5,223,483 A * | 6/1993 | Thomas | C07K 14/501 435/69.4 |
| 5,323,907 A | 6/1994 | Kalvelage | |
| 5,510,329 A * | 4/1996 | Belkin | A61K 38/1825 514/16.5 |
| 5,624,893 A * | 4/1997 | Yanni | A61K 31/00 514/17.2 |
| 6,780,837 B1 * | 8/2004 | LaVail | C07K 14/475 424/85.1 |
| 7,595,296 B1 | 9/2009 | Blaber et al. | |
| 7,659,379 B1 | 2/2010 | Blaber et al. | |
| 7,696,171 B1 | 4/2010 | Blaber et al. | |
| 7,776,825 B1 | 8/2010 | Blaber et al. | |
| 7,790,682 B1 | 9/2010 | Blaber et al. | |
| 8,119,776 B1 | 2/2012 | Blaber et al. | |
| 8,153,770 B1 | 4/2012 | Blaber et al. | |
| 8,153,771 B1 | 4/2012 | Blaber et al. | |
| 8,461,111 B2 * | 6/2013 | Blaber | A61K 38/18 514/9.1 |
| 2005/0227929 A1 | 10/2005 | Masferrer | |
| 2009/0136445 A1 | 5/2009 | Wong et al. | |
| 2010/0298220 A1 | 11/2010 | Blaber et al. | |
| 2011/0224404 A1 | 9/2011 | Blaber et al. | |
| 2013/0130983 A1 | 5/2013 | Blaber et al. | |

FOREIGN PATENT DOCUMENTS

| | | |
|---|---|---|
| EP | 0791576 A2 | 8/1997 |
| WO | WO-9955861 A2 | 11/1999 |
| WO | WO-2006105315 A2 | 10/2006 |
| WO | WO-2015048188 A2 | 4/2015 |
| WO | WO 2015/198175 | * 12/2015 |

OTHER PUBLICATIONS

Elhalis et al., Ocul Surf., 8(4):173-1884, 2010.*
Burstein, J Ocul Pharmacol, 3(3):263-77, Fall 1987.*
Caruelle et al. Immunological study of acidic fibroblast growth factor (aFGF) distribution in the eye. J Cell Biochem 39(2):117-128 (1989).
Dannowski et al. Lipid-mediated gene transfer of acidic fibroblast growth factor into human corneal endothelial cells. Exp Eye Res. 80(1):93-101 (2005).
Dubey et al. Spackling the crack: stabilizing human fibroblast growth factor-1 by targeting the N and C terminus beta-strand interactions. J Mol Biol 371(1):256-268 (2007).
Fredj-Reygrobellet et al. Effects of aFGF and bFGF on wound healing in rabbit corneas. Curr Eye Res 6(10):1205-1209 (1987).
Gospodarowicz et al. Stimulation of corneal endothelial cell proliferations in vitro by fibroblast and epidermal growth factors. Exp Eye Res 25:75-89 (1977).
Grant et al. Effects of epidermal growth factor, fibroblast growth factor, and transforming growth factor-beta on corneal cell chemotaxis. Invest Ophthalmol Vis Sci 33(12):3292-3301 (1992).
Jiang et al. Coated microneedles for drug delivery to the eye. Invest Ophthalmol Vis Sci 48(9):4038-4043 (2007).
Kim et al. Application of FGF-2 to modulate herpetic stromal keratitis. Curr Eye Res 31(12):1021-1028 (2006).
Koevary. Pharmacokinetics of topical ocular drug delivery: potential uses for the treatment of diseases of the posterior segement and beyond. Curr. Drug Metab. 4(3):213-222 (2003).

(Continued)

*Primary Examiner* — Marianne P Allen
(74) *Attorney, Agent, or Firm* — Wilson Sonsini Goodrich & Rosati

(57) ABSTRACT

Described herein are modified fibroblast growth factors (FGFs), pharmaceutical compositions, ophthalmic formulations, and medicaments that include such modified FGFs, and methods of using such modified FGFs to treat ocular diseases, disorders, or conditions.

5 Claims, 9 Drawing Sheets
Specification includes a Sequence Listing.

(56) References Cited

OTHER PUBLICATIONS

Landshman et al. Regeneration of cat corneal endothelium induced in vivo by fibroblast growth factor. Exp Eye Res 45:805-811 (1987).
Meduri et al. Effect of basic fibroblast growth factor on corneal epithelial healing after photorefractive keratectomy. J Refract Surg 28(3):220-223 (2012).
Noji et al. Expression pattern of acidic and basic fibroblast growth factor genes in adult rat eyes. Biochem Biophys Res Commu 168(1):343-349 (1990).
Okumura et al. Enhancement of corneal endothelium wound healing by Rho-associated kinase (ROCK) inhibitor eye drops. Br J Ophthalmol 95(7):1006-1009 (2011).
Ornitz el al. Receptor specificity of the fibroblast growth factor family. J Biol Chem 271(25):15292-15297 (1996).
Ramos et al. FGF-1 reverts epithelial-mesenchymal transition induced by TGF-{beta}1 through MAPK/ERK kinase pathway. Am J Physiol Lung Cell Mol Physiol 299:L222-L231 (2010).
Rieck et al. Human recombinant bFGF stimulates corneal endothelial wound healing in rabbits. Curr Eye Res 11(12):1161-1172 (1992).
Schulz et al. Acidic and basic FGF in ocular media and lens: implications for lens polarity and growth patterns. Development 118(1):117-126 (1993).
Thalmann-Goetsch et al. Comparative study on the effects of different growth factors on migration of bovine corneal endothelial cells during wound healing. Acta Ophthalmol Scand 75(5):490-495 (1997).
Wilson et al. Epidermal growth factor, transforming growth factor alpha, transforming growth factor beta, acidic fibroblast growth factor, basic fibroblast growth factor, and interleukin-1 proteins in the cornea. Exp Eye Res 59:53-72 (1994).
Xu et al. Diversification of the structural determinants of fibroblast growth factor—heparin interactions: implications for binding specificity J Biol Chem 287(47):40061-40673 (2012).
Kaye et al. The Fine Structure of the Rabbit Cornea and the Uptake and Transport of Colloidal Particles by the Cornea in Vivo. The Journal of Cell Biology 12:457-479 (1962).
Meduri et al. Effect of basic fibroblast growth factor in transgenic mice: corneal epithelial healing process after excimer laser photoablation. Ophthalmologica 223(2):139-144 (2009).
Dubey et al. Redesigning symmetry-related "mini-core" regions of FGF-1 to increase primary structure symmetry: thermodynamic and functional consequences of structural symmetry. Protein Sci 14(9):2315-2323 (2005).
Ortega et al. Conversion of cysteine to serine residues alters the activity, stability, and heparin dependence of acidic fibroblast growth factor. J Biol Chem 266:5842-5846 (1991).
Brych et al. Structure and stability effects of mutations designed to increase the primary sequence symmetry within the core region of a β-trefoil. Protein Science 10:2587-2599 (2001).
Culajay et al. Thermodynamic Characterization of Mutants of Human Fibroblast Growth Factor 1 with an Increased Physiological Half-Life. Biochemistry 39(24):7153-7158 (2000).
Lee et al. A Logical OR Redundancy within the Asx-Pro-Asx-Gly Type I β-Turn Motif. JMB 377:1251-1264 (2008).
Lee et al. Structural basis of conserved cysteine in the fibroblast growth factor family: evidence for a vestigial half-cystine. J Mol Biol 393(1):128-139 (2009).
Xia et al. Mutation Choice to Eliminate Buried Free Cysteines in Protein Therapeutics. J Pharm Sci 104:566-576 (2015).
Xia et al. Pharmacokinetic properties of 2nd-generation fibroblast growth factor-1 mutants for therapeutic application. PLoS one 7(11):e48210 (12 pgs) (2012).

\* cited by examiner

SEQUENCE LISTING

<160> NUMBER OF SEQ ID NOS: 4

<210> SEQ ID NO 1
<211> LENGTH: 140
<212> TYPE: PRT
<213> ORGANISM: Homo Sapiens

<400> SEQUENCE: 1

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 2
<211> LENGTH: 140
<212> TYPE: PRT
<213> ORGANISM: Homo Sapiens

<400> SEQUENCE: 2

Phe Asn Leu Pro Pro Gly Asn Tyr Lys Lys Pro Val Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
        115                 120                 125

Ala Ile Leu Phe Leu Val Leu Pro Val Ser Ser Asp
    130                 135                 140

<210> SEQ ID NO 3

```
<211> LENGTH: 140
<212> TYPE: PRT
<213> ORGANISM: Homo Sapiens

<400> SEQUENCE: 3

Phe Asn Leu Pro Pro Gly Asn Tyr Lys Lys Pro Lys Leu Leu Tyr Ser
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Cys Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
            115                 120                 125

Ala Ile Leu Phe Leu Pro Leu Pro Val Ser Ser Asp
        130                 135                 140

<210> SEQ ID NO 4
<211> LENGTH: 140
<212> TYPE: PRT
<213> ORGANISM: Homo Sapiens

<400> SEQUENCE: 4

Phe Asn Leu Pro Pro Gly Asn Tyr Lys Lys Pro Val Leu Leu Tyr Ser
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Cys Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Val Lys Arg Gly Pro Arg Thr His Tyr Gly Gln Lys
            115                 120                 125

Ala Ile Leu Phe Leu Pro Val Leu Pro Val Ser Ser Asp
        130                 135                 140
```

MODIFIED FIBROBLAST GROWTH FACTORS FOR THE TREATMENT OF OCULAR DISORDERS

CROSS REFERENCE

The present application is a national stage entry of PCT/US2014/057302, filed Sep. 24, 2014, which claims the benefit of U.S. Provisional Application No. 61/882,561, filed Sep. 25, 2013, the entire contents of which are hereby incorporated by reference.

SEQUENCE LISTING

The instant application contains a Sequence Listing which has been submitted in ASCII format via EFS-Web and is hereby incorporated by reference in its entirety. Said ASCII copy, created on Sep. 16, 2014, is named 45341_702_831_SL.txt and is 5,430 bytes in size.

FIELD OF THE INVENTION

Described herein are modified fibroblast growth factors (FGFs), pharmaceutical compositions and medicaments that include such modified FGFs, and methods of using such modified FGFs to treat ocular diseases, disorders, or conditions.

BACKGROUND OF THE INVENTION

Diseases of and injuries to the eyes can be severely debilitating, and occur in a wide variety of forms. One class of ocular disease, corneal endothelial dystrophies, is characterized by a progressive, non-inflammatory degeneration of the endothelium. Examples of corneal endothelial dystrophies are Fuch's dystrophy (FD), congenital hereditary endothelial dystrophy 1 or 2, and posterior polymorphous corneal dystrophy. FD is the most common and is estimated to affect approximately 4% of the U.S. population over the age of 40 (Schmedt et al. *Experimental eye research.* 2012; 95(1):24-34). FD has relatively late onset and is slowly progressive; many patients will ultimately need penetrating keratoplasty. It is estimated that FD cases account for 10-25% of the 32000 cornea transplants in the U.S. (Klintworth, *Orphanet journal of rare diseases.* 2009; 4:7), a higher proportion in the U.K. (Keenan et al. *Archives of ophthalmology.* 2012; 130(5):621-8) and the majority of the endothelial keratoplasty procedures. In 2008, 17,468 endothelial keratoplasty procedures were performed in the US (Li J Y et al. International ophthalmology clinics. 2010; 50(3):101-12).

SUMMARY OF THE INVENTION

Provided herein are methods of treating or preventing an ocular disease, disorder or condition in a mammal comprising administering to the mammal a modified fibroblast growth factor (FGF). In some embodiments, the modified FGF is an FGF that contains one or more mutations. In some embodiments, the modified FGF is thermostable. In some embodiments, the modified FGF comprises a reduced number of reactive thiols. In some embodiments, the modified FGF is a modified FGF-1 or a modified FGF-2. In some embodiments, the modified FGF is a modified FGF-1. In some embodiments, the modified FGF-1 is a human FGF-1 (SEQ ID NO: 1) comprising one or more mutations at positions 12, 134, or 117 of human FGF-1. In some embodiments, the modified FGF-1 is a human FGF-1 comprising one or more mutations selected from Lys12Val, Pro134Val, and Cys117Val. In some embodiments, the modified FGF-1 is a human FGF-1 comprising the following mutations: Lys12Val, Pro134Val, and Cys117Val. In some embodiments, the modified FGF comprises the sequence of SEQ ID NO: 2.

In some embodiments, the method is performed without administering heparin to said mammal.

In some embodiments, the ocular disease, disorder or condition is a disease, disorder, or condition of the cornea or ocular surface.

In some embodiments, the ocular disease, disorder or condition is a disease, disorder, or condition of the corneal endothelium. In some embodiments, the said disease, disorder, or condition of the corneal endothelium is Fuch's dystrophy, bullous keratopathy, congenital hereditary endothelial dystrophy 1, congenital hereditary endothelial dystrophy 2, posterior polymorphous corneal dystrophy, or a dry eye syndrome. In some embodiments, the ocular disease, disorder or condition is Fuch's dystrophy.

In some embodiments, the ocular disease, disorder or condition is a disease, disorder, or condition of the corneal epithelium. In some embodiments, the condition of the corneal epithelium is a dry eye syndrome or corneal epithelial damage from corneal surgery or transplantation. In some embodiments, the corneal surgery is photorefractive keratotomy (PRK) or laser-assisted in situ keratomileusis (LASIK). In some embodiments, the said ocular disease, disorder or condition is a disease, disorder, or condition of the corneal stroma. In some embodiments, the disease, disorder, or condition of the corneal stroma is keratoconus, lattice corneal dystrophy, granular corneal dystrophy, macular corneal dystrophy, Schnyder crystalline corneal dystrophy, congenital stromal corneal dystrophy, or fleck corneal dystrophy.

In some embodiments, the modified FGF is administered topically, by microneedle into the cornea, or intracamerally. In some embodiments, the modified FGF is administered by an eye drop.

Additional embodiments relate to a method of treating or preventing a disease, disorder or condition of the cornea in a mammal comprising administering to the mammal a pharmaceutical composition comprising a modified fibroblast growth factor (e.g., a modified FGF-1 such as one comprising the sequence of SEQ ID NO: 2) and a pharmaceutically acceptable carrier, excipient, or diluent.

In some embodiments, the modified FGF is an FGF that contains one or more mutations. In some embodiments, the modified FGF is thermostable. In some embodiments, the modified FGF comprises a reduced number of reactive thiols. In some embodiments, the modified FGF is a modified FGF-1 or a modified FGF-2. In some embodiments, the modified FGF is a modified FGF-1. In some embodiments, the modified FGF-1 is a human FGF-1 (SEQ ID NO: 1) comprising one or more mutations at positions 12, 134, or 117 of human FGF-1. In some embodiments, the modified FGF-1 is a human FGF-1 comprising one or more mutations selected from Lys12Val, Pro134Val, and Cys117Val. In some embodiments, the modified FGF-1 is a human FGF-1 comprising the following mutations: Lys12Val, Pro134Val, and Cys117Val. In some embodiments, the modified FGF comprises the sequence of SEQ ID NO: 2.

In some embodiments, the ocular disease, disorder or condition is a disease, disorder, or condition of the cornea or ocular surface.

In some embodiments, the ocular disease, disorder or condition is a disease, disorder, or condition of the corneal endothelium. In some embodiments, the said disease, disorder, or condition of the corneal endothelium is Fuch's dystrophy, bullous keratopathy, congenital hereditary endothelial dystrophy 1, congenital hereditary endothelial dystrophy 2, posterior polymorphous corneal dystrophy, or a dry eye syndrome. In some embodiments, the ocular disease, disorder or condition is Fuch's dystrophy.

In some embodiments, the ocular disease, disorder or condition is a disease, disorder, or condition of the corneal epithelium. In some embodiments, the condition of the corneal epithelium is a dry eye syndrome or corneal epithelial damage from corneal surgery or transplantation. In some embodiments, the corneal surgery is photorefractive keratotomy (PRK) or laser-assisted in situ keratomileusis (LASIK). In some embodiments, the said ocular disease, disorder or condition is a disease, disorder, or condition of the corneal stroma. In some embodiments, the disease, disorder, or condition of the corneal stroma is keratoconus, lattice corneal dystrophy, granular corneal dystrophy, macular corneal dystrophy, Schnyder crystalline corneal dystrophy, congenital stromal corneal dystrophy, or fleck corneal dystrophy In some embodiments, the pharmaceutical composition is free of heparin. In some embodiments, the pharmaceutical composition is a liquid ophthalmic formulation. In some embodiments, the ophthalmic formulation is administered topically, by microneedle into the cornea, or intracamerally. In some embodiments, the ophthalmic formulation is administered by an eye drop.

Further embodiments relate to a method of transplanting corneal cells to a mammal comprising: 1) enhancing the success of cell transplantation by treating said corneal cells to be transplanted with a modified fibroblast growth factor (e.g., a modified FGF-1 such as one comprising the sequence of SEQ ID NO: 2) prior to, during or after transplanting said corneal cells to said mammal.

In some embodiments, the corneal cells comprise cells from donor corneal tissue within the donor cornea. In some embodiments, the corneal cells comprise cells derived from progenitor cells.

In some embodiments, the modified FGF-1 comprises the sequence of SEQ ID NO: 2.

Additional embodiments relate to an ophthalmic formulation comprising a modified FGF (e.g., a modified FGF-1 such as one comprising the sequence of SEQ ID NO: 2) and a pharmaceutically acceptable (e.g., ophthalmologically suitable or acceptable) carrier, excipient, or diluent. In some embodiments, the modified FGF is an FGF that contains one or more mutations. In some embodiments, the modified FGF is thermostable. In some embodiments, the modified FGF comprises a reduced number of reactive thiols. In some embodiments, the modified FGF is a modified FGF-1 or a modified FGF-2. In some embodiments, the modified FGF is a modified FGF-1. In some embodiments, the modified FGF-1 is a human FGF-1 (SEQ ID NO: 1) comprising one or more mutations at positions 12, 134, or 117 of human FGF-1. In some embodiments, the modified FGF-1 is a human FGF-1 comprising one or more mutations selected from Lys12Val, Pro134Val, and Cys117Val. In some embodiments, the modified FGF-1 is a human FGF-1 comprising the following mutations: Lys12Val, Pro134Val, and Cys117Val. In some embodiments, the modified FGF comprises the sequence of SEQ ID NO: 2.

In some embodiments, the said ophthalmic formulation is free of heparin. In some embodiments, the ophthalmic formulation is a liquid formulation. Further embodiments relate to a kit comprising the ophthalmic formulation and a container.

Additional embodiments relate to a method of modulating the activity of one or more fibroblast growth factor receptors (FGFRs) in a corneal endothelial cell comprising contacting said corneal endothelial cell with a modified FGF. In some embodiments, the modified FGF is an FGF that contains one or more mutations. In some embodiments, the modified FGF is thermostable. In some embodiments, the modified FGF comprises a reduced number of reactive thiols. In some embodiments, the modified FGF is a modified FGF-1 or a modified FGF-2. In some embodiments, the modified FGF is a modified FGF-1. In some embodiments, the modified FGF-1 is a human FGF-1 (SEQ ID NO: 1) comprising one or more mutations at positions 12, 134, or 117 of human FGF-1. In some embodiments, the modified FGF-1 is a human FGF-1 comprising one or more mutations selected from Lys12Val, Pro134Val, and Cys117Val. In some embodiments, the modified FGF-1 is a human FGF-1 comprising the following mutations: Lys12Val, Pro134Val, and Cys117Val. In some embodiments, the modified FGF comprises the sequence of SEQ ID NO: 2.

In some embodiments, the modulating increases the activity of said one or more FGFRs. In some embodiments, the modulating increases the migration and/or proliferation of said corneal endothelial cell(s).

In some aspects, provided herein is a method of treating or preventing an ocular disease, disorder or condition in a mammal comprising administering to the mammal a modified FGF-1 comprising one or more mutations of human FGF-1 at positions 12, 16, 66, 117, and 134. In some embodiments, the modified FGF-1 comprises one or more mutations selected from the group consisting of: Lys12Val, Pro134Val, Ala66Cys, Cys117Val, and Pro134Val. In some embodiments, the sequence of the modified FGF-1 comprises the sequence of SEQ ID NO: 2. In some embodiments, the sequence of the modified FGF-1 comprises a sequence with 85%, 86%, 87%, 88%, 89%, 90%, 91%, 92%, 93%, 94%, 95%, 96%, 97%, 98%, 99% or 100% sequence identity to SEQ ID NO: 2. In some embodiments, the sequence of the modified FGF-1 comprises the sequence of SEQ ID NO: 3. In some embodiments, the sequence of the modified FGF-1 comprises a sequence with 85%, 86%, 87%, 88%, 89%, 90%, 91%, 92%, 93%, 94%, 95%, 96%, 97%, 98%, 99% or 100% sequence identity to SEQ ID NO: 3. In some embodiments, the sequence of the modified FGF-1 comprises the sequence of SEQ ID NO: 4. In some embodiments, the sequence of the modified FGF-1 comprises a sequence with 85%, 86%, 87%, 88%, 89%, 90%, 91%, 92%, 93%, 94%, 95%, 96%, 97%, 98%, 99% or 100% sequence identity to SEQ ID NO: 4. In some embodiments, the numbering of the amino acid residues of SEQ ID NO:1, SEQ ID NO:2, SEQ ID NO:3, and SEQ ID NO: 4 are based on the 140 amino acid numbering nomenclature for FGF-1. In some embodiments, the modified FGF-1 is thermostable. In some embodiments, the modified FGF-1 comprises a reduced number of reactive thiols. In some embodiments, the method is performed without administering heparin to the mammal. In some embodiments, the ocular disease, disorder or condition is a disease, disorder, or condition of the cornea or ocular surface. In some embodiments, the ocular disease, disorder or condition is a disease, disorder, or condition of the corneal endothelium. In some embodiments, the disease, disorder, or condition of the corneal endothelium is Fuch's dystrophy, bullous keratopathy, congenital hereditary endothelial dystrophy 1, congenital hereditary endothelial dystrophy 2, posterior polymorphous corneal dystrophy, or a dry eye syndrome. In some embodiments, the ocular disease, disorder or condition is Fuch's dystrophy. In some embodiments, the ocular disease, disorder or condition is a disease, disorder, or condition of the corneal epithelium. In some embodiments, the condition of the corneal epithelium is a dry eye syndrome or corneal epithelial damage from corneal surgery or transplantation. In some embodiments, the corneal surgery is photorefractive keratotomy (PRK) or laser-assisted in situ keratomileusis (LASIK). In some embodiments, the ocular disease, disorder or condition is a disease, disorder, or condition of the corneal stroma. In some embodiments, the disease, disorder, or condition of the corneal stroma is keratoconus, lattice corneal dystrophy, granular corneal dystrophy, macular corneal dystrophy, Schnyder crystalline corneal dystrophy, congenital stromal corneal dystrophy, or fleck corneal dystrophy. In some embodiments, the modified FGF-1 is administered topically, by microneedle into the cornea, or intracamerally. In some embodiments, the modified FGF-1 is administered by an eye drop.

In some aspects provided herein is a method of treating or preventing a disease, disorder or condition of the cornea in a mammal comprising administering to the mammal a pharmaceutical composition comprising: a modified FGF-1 comprising one or more mutations of human FGF-1 at positions 12, 16, 66, 117, and 134; and a pharmaceutically acceptable carrier, excipient, or diluent. In some embodiments, the modified FGF-1 comprises one or more mutations selected from the group consisting of: Lys12Val, Pro134Val, Ala66Cys, Cys117Val, and Pro134Val. In some embodiments, the modified FGF-1 comprises the sequence of SEQ ID NO: 2. In some embodiments, the modified FGF-1 comprises the sequence of SEQ ID NO: 3. In some embodiments, the modified FGF-1 comprises the sequence of SEQ ID NO: 4. In some embodiments, the modified FGF-1 is thermostable. In some embodiments, the modified FGF-1 comprises a reduced number of reactive thiols. In some embodiments, the pharmaceutical composition is free of heparin. In some embodiments, the ocular disease, disorder or condition is a disease, disorder, or condition of the cornea or ocular surface. In some embodiments, the ocular disease, disorder or condition is a disease, disorder, or condition of the corneal endothelium. In some embodiments, the disease, disorder, or condition of the corneal endothelium is Fuch's dystrophy, bullous keratopathy, congenital hereditary endothelial dystrophy 1, congenital hereditary endothelial dystrophy 2, posterior polymorphous corneal dystrophy, or a dry eye syndrome. In some embodiments, the ocular disease, disorder or condition is Fuch's dystrophy. In some embodiments, ocular disease, disorder or condition is a disease, disorder, or condition of the corneal epithelium. In some embodiments, the condition of the corneal epithelium is a dry eye syndrome or corneal epithelial damage from corneal surgery or transplantation. In some embodiments, the corneal surgery is photorefractive keratotomy (PRK) or laser-assisted in situ keratomileusis (LASIK). In some embodiments, the ocular disease, disorder or condition is a disease, disorder, or condition of the corneal stroma. In some embodiments, the disease, disorder, or condition of the corneal stroma is keratoconus, lattice corneal dystrophy, granular corneal dystrophy, macular corneal dystrophy, Schnyder crystalline corneal dystrophy, congenital stromal corneal dystrophy, or fleck corneal dystrophy. In some embodiments, the pharmaceutical composition is a liquid ophthalmic formulation. In some embodiments, the ophthalmic formulation is administered topically, by microneedle into the cornea, or intracamerally. In some embodiments, the ophthalmic formulation is administered by an eye drop.

In some aspects provided herein is a method of transplanting corneal cells to a mammal comprising enhancing the success of cell transplantation by treating the corneal cells to be transplanted with a modified FGF-1 prior to, during or after transplanting the corneal cells to the mammal, the modified FGF-1 comprising one or more mutations of human FGF-1 at positions 12, 16, 66, 117, and 134. In some embodiments, the corneal cells comprise cells from donor corneal tissue within the donor cornea. In some embodiments, the corneal cells comprise cells derived from progenitor cells. In some embodiments, the modified FGF-1 comprises one or more mutations selected from the group consisting of: Lys12Val, Pro134Val, Ala66Cys, Cys117Val, and Pro134Val. In some embodiments, the modified FGF-1 comprises the sequence of SEQ ID NO: 2. In some embodiments, the modified FGF-1 comprises the sequence of SEQ ID NO: 3. In some embodiments, the modified FGF-1 comprises the sequence of SEQ ID NO: 4.

In some aspects provided herein is an ophthalmic formulation comprising: a modified FGF-1 comprising one or more mutations of human FGF-1 at positions 12, 16, 66, 117, and 134; and a pharmaceutically acceptable carrier, excipient, or diluent. In some embodiments, the modified FGF-1 comprises one or more mutations selected from the group consisting of: Lys12Val, Pro134Val, Ala66Cys, Cys117Val, and Pro134Val. In some embodiments, the modified FGF-1 comprises the sequence of SEQ ID NO: 2. In some embodiments, the modified FGF-1 comprises the sequence of SEQ ID NO: 3. In some embodiments, the modified FGF-1 comprises the sequence of SEQ ID NO: 4. In some embodiments, the modified FGF-1 is thermostable. In some embodiments, the modified FGF-1 comprises a reduced number of reactive thiols. In some embodiments, the ophthalmic formulation is free of heparin. In some embodiments, the ophthalmic formulation is a liquid formulation.

In some aspects provided herein is a kit comprising: an ophthalmic formulation comprising: a modified FGF-1 comprising one or more mutations of human FGF-1 at positions 12, 16, 66, 117, and 134; and a pharmaceutically acceptable carrier, excipient, or diluent; and a container. In some embodiments, the modified FGF-1 comprises one or more mutations selected from the group consisting of: Lys12Val, Pro134Val, Ala66Cys, Cys117Val, and Pro134Val. In some embodiments, the modified FGF-1 comprises the sequence of SEQ ID NO: 2. In some embodiments, the modified FGF-1 comprises the sequence of SEQ ID NO: 3. In some embodiments, the modified FGF-1 comprises the sequence of SEQ ID NO: 4. In some embodiments, the modified FGF-1 is thermostable. In some embodiments, the modified FGF-1 comprises a reduced number of reactive thiols. In some embodiments, the ophthalmic formulation is free of heparin. In some embodiments, the ophthalmic formulation is a liquid formulation.

In some aspects provided herein is a method of modulating the activity of one or more fibroblast growth factor receptors in a corneal endothelial cell comprising contacting the corneal endothelial cell with a modified FGF-1 comprising one or more mutations of human FGF-1 at positions 12, 16, 66, 117, and 134. In some embodiments, the modified FGF-1 comprises one or more mutations selected from the group consisting of: Lys12Val, Pro134Val, Ala66Cys, Cys117Val, and Pro134Val. In some embodiments, the modified FGF-1 comprises the sequence of SEQ ID NO: 2. In some embodiments, the modified FGF-1 comprises the sequence of SEQ ID NO: 3. In some embodiments, the modified FGF-1 comprises the sequence of SEQ ID NO: 4. In some embodiments, the modified FGF-1 is thermostable. In some embodiments, the modified FGF-1 comprises a reduced number of reactive thiols. In some embodiments, the modulating increases the activity of the one or more FGFRs. In some embodiments, the modulating increases the proliferation of the corneal endothelial cell.

In some aspects provided herein is a method of preventing scarring during tissue regeneration comprising administering a modified FGF-1 comprising one or more mutations of human FGF-1 at positions 12, 16, 66, 117, and 134. In some embodiments, the modified FGF-1 comprises one or more mutations selected from the group consisting of: Lys12Val, Pro134Val, Ala66Cys, Cys117Val, and Pro134Val. In some embodiments, the modified FGF-1 comprises the sequence of SEQ ID NO: 2. In some embodiments, the modified FGF-1 comprises the sequence of SEQ ID NO: 3. In some embodiments, the modified FGF-1 comprises the sequence of SEQ ID NO: 4. In some embodiments, the modified FGF-1 is adminstered in a suitable ohpthalmic foruulation. In some embodiments, the modified FGF-1 is administered to a mammal after undergoing a trabeculectomy.

All publications and patent applications mentioned in this specification are herein incorporated by reference in their entireties to the same extent as if each individual publication or patent application was specifically and individually indicated to be incorporated by reference.

DETAILED DESCRIPTION

Figure 1A:
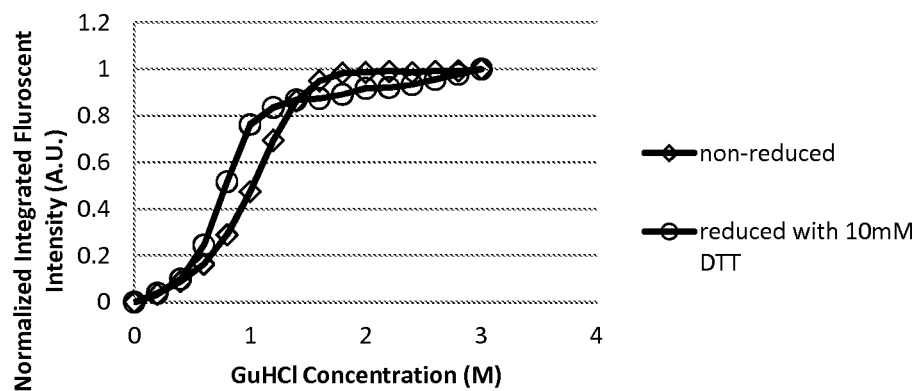
FIG. 1A depicts, as a non-limiting example, an isothermal denaturation curve of a modified FGF-1 protein with the sequence of SEQ ID NO: 3.

Provided herein are modified fibroblast growth factors (FGFs), pharmaceutical compositions and medicaments that include such modified peptides, and methods of using such modified FGFs to treat ocular diseases, disorders, or conditions. In some embodiments, the modified FGFs described herein can be used to treat corneal disease, disorders and conditions, e.g., corneal endothelial dystrophies such as Fuch's dystrophy (FD).

Growth factors are key regulators of the proliferation and migration of the cells of the cornea and associated structures. Fibroblast growth factors (FGFs) comprise a large family of evolutionarily conserved polypeptides involved in a variety of biological processes including morphogenesis, angiogenesis, and tissue remodeling as well as in the pathogenesis of numerous diseases. The various members of this family stimulate the proliferation of a wide spectrum of cells, including those deriving from mesenchymal, endothelial, epithelial and neuroectodermal origin. Corneal epithelial and endothelial cells are responsive to growth factors including the fibroblast growth factor (FGF) family. The biological response of cells to FGF is mediated through specific cell surface receptors (FGFRs). FGF is chemotactic for corneal cells (Grant et al. (1992). *Invest Ophthalmol Vis Sci* 33(12): 3292-3301) and promotes the healing of corneal wounds in animals (Fredj-Reygrobellet et al. (1987). *Curr Eye Res* 6(10): 1205-1209) as well as reducing lesion severity in herpetic keratitis (Kim et al. (2006). *Curr Eye Res* 31(12): 1021-1028). In addition, the application of FGF-2 (basic FGF) can accelerate the healing of corneal epithelial wounds following photorefractive keratotomy (PRK) (Meduri et al. (2012). *J Refract Surg* 28(3): 220-223). FGF has also been show to stimulate corneal fibroblasts (Woost et al. (1985). *Exp Eye Res* 40(1): 47-60).

The driving cause of FD and other corneal dystrophies is unknown. At the cellular level, these conditions are characterized by a progressive loss of corneal endothelial cells (CECs). The CECs form a barrier between the aqueous humor and the corneal stroma and actively pump ions. This maintains fluid balance in the cornea, counteracting the tendency of the glycosaminoglycan (GAG)-rich stroma to absorb fluid and maintaining the proper architecture for optical function. Aging results in decreases in the number of CECs, and in FD dystrophy the number of cells decreases to the point where the barrier function is compromised. Failure of the CECs barrier and ion pumping activity leads to corneal edema, degradation of the optical qualities of the cornea, and poor vision.

Treatment of endothelial dysfunction currently utilizes the transplantation of CECs either as a whole corneal transplant or transplantation of the endothelial layer via Descemet's stripping endothelial keratoplasty (DSEK) (Anshu et al. *Survey of ophthalmology.* 2012; 57(3):236-52), Descemet's membrane endothelial keratoplasty (DMEK) (Price et al. *Current opinion in ophthalmology.* 2013; 24(4):329-35) or related procedures. Even after transplantation, the number of CECs in the transplant continues to decrease (Patel *Experimental eye research.* 2012; 95(1):40-7) and repeat transplants are sometimes needed. Transplantation is an option of last resort as donor tissue is in short supply, the surgery requires a high level of skill on the part of the surgeon, and a there is a significant complication rate.

While the CECs do not repopulate or renew in either normal or FD patients, there is evidence that 1) cells from the peripheral corneal endothelium can migrate centrally (He et al. *Stem cells.* 2012; 30(11):2523-34) and 2) cells of the peripheral corneal endothelium (Mimura et al. *Investigative ophthalmology & visual science.* 2005; 46(10):3645-8; Yamagami et al. *Ophthalmology.* 2007; 114(3):433-9; Yu et al. *Journal of biomedicine & biotechnology.* 2011; 2011: 412743) or TM (Whikehart et al. *Molecular vision.* 2005; 11:816-24; McGowan et al. *Molecular vision.* 2007; 13:1984-2000) may contain a progenitor population (Yu et al. *Journal of biomedicine & biotechnology.* 2011; 2011: 412743). Therefore, treatments that increase migration and proliferation of endothelial cells may improve barrier function in the central cornea by providing additional cells from the periphery. A pharmaceutical treatment that stimulates the migration and or proliferation of CECs can reduce corneal edema in these patients and delay or eliminate the need for corneal transplantation.

CECs are responsive to a number of growth factors including several of the FGF family. FGFs stimulate a family seven FGF receptor isoforms, and each FGF stimulates a different pattern of receptors to achieve its specific effect (Ornitz et al. *The Journal of biological chemistry.* 1996; 271(25):15292-7; Zhang et al. *The Journal of biological chemistry.* 2006; 281(23):15694-700). FGF-1 (also referred to as acidic FGF) is unique among FGFs in that it binds to and stimulates all seven FGF receptor isoforms (Ornitz et al. *The Journal of biological chemistry.* 1996; 271(25):15292-7). FGF-1 is expressed in the cornea during development (Lovicu et al. *Current eye research.* 1997; 16(3):222-30), in the adult (Caruelle et al. *Journal of cellular biochemistry.* 1989; 39(2):117-28), and is found in the aqueous humor (Schulz et al. *Development.* 1993; 118(1): 117-26). FGF-1 is known to stimulate migration (Lee et al. *Investigative ophthalmology & visual science.* 2006; 47(4): 1376-86) and proliferation in bovine (Thalmann-Goetsch et al. *Acta ophthalmologica Scandinavica.* 1997; 75(5):490-5) and human (Dannowski et al. *Experimental eye research.* 2005; 80(1):93-101) CECs. Therefore, without being bound by theory, it is believed that exogenously supplied FGF-1 can promote the migration and proliferation of CECs in vivo and can be useful as a therapeutic for endothelial dystrophies.

However, there are several issues that complicate effective realization of FGF-1 as a therapeutic. First, it has relatively poor thermal stability in the absence of heparin, which negatively impacts potency and storage lifetimes as well as its potential half-life in vivo. Although inclusion of heparin in the formulation can increase stability, it negatively impacts the binding of FGF-1 to tissue heparans. These are critical issues impacting efficacy and frequency of administration. In addition, heparin is more expensive than FGF-1 to produce, is derived from pigs (with the potential for infectious agents), is naturally heterogeneous in structure and function, and has anti-coagulant activity, which can prevent safely achieving optimal dose levels. Furthermore, some individuals are immunologically sensitized to heparin, which on subsequent exposure can lead to heparin-induced thrombosis (Prechel et al. *Seminars in Thrombostasis and Hemostasis.* 2012; 38:483-96).

Provided herein are modified FGFs, pharmaceutical compositions, and ophthalmic formulations thereof, suitable for the methods described herein. In some embodiments, the modified FGFs, pharmaceutical compositions, and ophthalmic formulations thereof useful for the treatment of ocular diseases, disorders, and conditions, such as those of the corneal endothelium, epithelium, and stroma.

The modified FGFs described herein are particularly advantageous for the methods and applications described herein. For example, the modified FGFs described herein can be administered without heparin in its pharmaceutical composition or formulation (e.g., an ophthalmic formulation), avoiding potential safety issues related to its biologic origin. In addition, avoidance of heparin allows the use of higher doses of the modified FGFs without complications resulting from local heparin-induced adverse events or pre-existing anti-heparin antibodies. Furthermore, in the absence of heparin, immediate binding of the modified FGF to tissue is maximized and systemic distribution is significantly reduced. The modified FGFs described herein are also advantage of having enhanced local sequestration and reduced redistribution kinetics, thus increasing the elimination half-life and mean residence time (MRT) at the site of delivery, and allowing for a reduced dosing frequency. This can be the result of modified FGFs described herein that have increased stability (e.g. thermostability), reduced number of buried free thiols, and/or increased effective heparan sulfate proteoglycan (HSPG) affinity.

CERTAIN TERMINOLOGY

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

The terms "treat," "treating" or "treatment" include alleviating, abating or ameliorating a disease, disorder or condition symptoms, preventing additional symptoms, ameliorating or preventing the underlying metabolic causes of symptoms, inhibiting the disease, disorder, or condition, e.g., arresting the development of the disease, disorder or condition, relieving the disease, disorder or condition, causing regression of the disease, disorder or condition, relieving a condition caused by the disease, disorder or condition, or stopping the symptoms of the disease, disorder or condition. The terms "treat," "treating" or "treatment", include, but are not limited to, prophylactic and/or therapeutic treatments.

The term "acceptable" or "pharmaceutically acceptable", with respect to a formulation, composition or ingredient, refers to having no persistent detrimental effect on the general health of the subject being treated or does not abrogate the biological activity or properties of the modified FGF described herein, and is relatively nontoxic.

The term "amelioration" of the symptoms of a particular disease, disorder or condition by administration of a particular modified FGF or pharmaceutical composition refers to any lessening of severity, delay in onset, slowing of progression, or shortening of duration, whether permanent or temporary, lasting or transient that can be attributed to or associated with administration of the modified FGF or pharmaceutical composition.

The term "combination" or "pharmaceutical combination" as used herein, means a product that results from the mixing or combining of more than one active ingredient and includes both fixed and non-fixed combinations of the active ingredients. The term "fixed combination" means that one active ingredient (e.g. a modified FGF) and a co-agent are both administered to a patient simultaneously in the form of a single entity or dosage. The term "non-fixed combination" means that one active ingredient (e.g. a modified FGF) and a co-agent are administered to a patient as separate entities either simultaneously, concurrently or sequentially with no specific intervening time limits, wherein such administration provides effective levels of the two agents in the body of the patient. The latter also applies to cocktail therapy, e.g. the administration of three or more active ingredients.

The term "pharmaceutical composition" as used herein refers to one or more modified FGFs with one or more other chemical components, such as carriers, stabilizers, diluents, dispersing agents, suspending agents, thickening agents, and/or excipients. The pharmaceutical composition facilitates administration of the modified FGF to an organism. Multiple techniques of administering a modified FGF exist in the art including, but not limited to: topical, ophthalmic, intraocular, periocular, intravenous, oral, aerosol, parenteral, and administration.

The term "carrier," as used herein, refers to relatively nontoxic chemical compounds or agents that facilitate the incorporation of an agent of interest (e.g., a modified FGF) into cells or tissues.

The term "diluent" refers to chemical compounds that are used to dilute the agent of interest (e.g., a modified FGF) prior to delivery. Diluents can also be used to stabilize agents because they can provide a more stable environment. Salts dissolved in buffered solutions (which also can provide pH control or maintenance) are utilized as diluents in the art, including, but not limited to a phosphate buffered saline solution.

The terms "co-administration" or the like, are meant to encompass administration of the selected agents (e.g., a modified FGF or composition thereof and a co-agent) to a single patient, and are intended to include treatment regimens in which the agents are administered by the same or different route of administration or at the same or different time.

The terms "effective amount" or "therapeutically effective amount," refer to a sufficient amount of a modified FGF, agent, combination or pharmaceutical composition described herein administered which will relieve to some extent one or more of the symptoms of the disease, disorder or condition being treated. The result can be reduction and/or alleviation of the signs, symptoms, or causes of a disease, or any other desired alteration of a biological system. For example, an "effective amount" for therapeutic uses is the amount of the modified FGF, agent, combination or pharmaceutical composition required to provide a desired pharmacologic effect, therapeutic improvement, or clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. It is understood that "an effect amount" can vary from subject to subject due to variation in metabolism of the modified FGF, combination, or pharmaceutical composition, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The term "prophylactically effective amount," refers that amount of a modified FGF, compound, agent, combination or pharmaceutical composition described herein applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "subject" or "patient" as used herein, refers to an animal, which is the object of treatment, observation or experiment. By way of example only, a subject may be, but is not limited to, a mammal including, but not limited to, a human.

The terms "enhance" or "enhancing" means to increase or prolong either in potency or duration a desired effect. By way of example, "enhancing" the effect of therapeutic agents singly or in combination refers to the ability to increase or prolong, either in potency, duration and/or magnitude, the effect of the agents on the treatment of a disease, disorder or condition. When used in a patient, amounts effective for this use will depend on the severity and course of the disease, disorder or condition, previous therapy, the patient's health status and response to the drugs, and the judgment of the treating physician.

The term "modulate," means to interact with a target (e.g., a FGF receptor) either directly or indirectly so as to alter the activity of the target, including, by way of example only, to enhance the activity of the target, to inhibit or antagonize the activity of the target, to limit the activity of the target, or to extend the activity of the target. In some embodiments, modified FGFs and pharmaceutical compositions described herein can modulate the activity of one or more respective targets (e.g., one or more FGF receptors). In some embodiments, the modified FGFs described herein modulate (e.g., increase) the activity of one or more FGF receptors on a cell (e.g., a corneal endothelial cell), resulting, e.g., in cell migration and/or cell proliferation.

As used herein, the term "target" refers to a biological molecule (e.g., a target protein or protein complex), such as an FGF receptor, or a portion of a biological molecule capable of being bound by a selective binding agent (e.g., a modified FGF) or pharmaceutical composition described herein. As used herein, the term "non-target" refers to a biological molecule or a portion of a biological molecule that is not selectively bound by a selective binding agent or pharmaceutical composition described herein.

The term "target activity" or "cell response" refers to a biological activity capable of being modulated by a modified FGF or any cellular response that results from the binding of a modified FGF to a FGF receptor. Certain exemplary target activities and cell responses include, but are not limited to, binding affinity, signal transduction, gene expression, cell migration, cell proliferation, cell differentiation, and amelioration of one or more symptoms associated with an ocular disease, disorder or condition.

The term "amino acid" refers to the molecules composed of terminal amine and carboxylic acid functional groups with a carbon atom between the terminal amine and carboxylic acid functional groups sometimes containing a side chain functional group attached to the carbon atom (e.g. a methoxy functional group, which forms the amino acid serine). Typically, amino acids are classified as natural and non-natural. Examples of natural amino acids include glycine, alanine, valine, leucine, isoleucine, proline, phenylananine, tyrosine, tryptophan, serine, threonine, cysteine, methionine, asparagine, glutamine, lysine, arginine, histidine, aspartate, and glutamate, among others. Examples of non-natural amino acids include L-3,4-dihydroxyphenylalanine, 2-aminobutyric acid, dehydralanine, g-carboxyglutamic acid, carnitine, gamma-aminobutyric acid, hydroxyproline, and selenomethionine, among others. In the context of this specification it should be appreciated that the amino acids may be the L-optical isomer or the D-optical isomer.

Modified Fibroblast Growth Factors (FGFs)

Embodiments disclosed herein relate to a modified FGF or a pharmaceutical composition (e.g., an ophthalmic formulation) comprising a modified FGF. A modified FGF, as used herein, refers to a wild-type or native FGF that includes a substitution or mutation of one or more different amino acid residues and/or one or more deletions of one or more amino acid residues and/or one or more additions of one or more amino acid residues. The wild-type or native FGF that includes the modification(s) can be any member of the FGF family, including FGF-1 (SEQ ID NO: 1), FGF-2, FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, FGF-22, and FGF-23, and FGF-24. FGFs stimulate a family seven FGF receptor isoforms, and each FGF stimulates a different pattern of receptors to achieve its specific effect (Ornitz et al. *The Journal of biological chemistry.* 1996; 271(25):15292-7; Zhang et al. *The Journal of biological chemistry.* 2006; 281(23):15694-700).

In some embodiments, the modified FGF is a modified FGF-1 or a modified FGF-2. In some embodiments, the modified FGF is a modified FGF-1. In some embodiments, modified FGF-1 is preferable since it binds to and stimulates all seven FGF receptor isoforms (Ornitz et al. *The Journal of biological chemistry.* 1996; 271(25):15292-7).

In some embodiments, the modified FGF is thermostable. As used herein, a thermostable FGF (e.g., a thermostable FGF-1) refers to an FGF having a modified amino acid sequence relative to the wild type FGF sequence that is also more stable than the wild type FGF under the same conditions. Examples of mutations capable of conferring thermostability to FGF (e.g., FGF-1) and methods for assessing thermostability are described, for example, in U.S. Pat. Nos. 7,790,682; 7,595,296; 7,696,171; 7,776,825; 7,659,379; 8,119,776; 8,153,770; 8,153,771; and 8,461,111; U.S. Patent Application Publication Nos. 2011/0224404, 2013/0130983; and in Xia et al. *PloS one.* 2012; 7(11):e48210. In some embodiments, positions 12 and/or 134 are mutated in FGF-1 to generate a modified FGF-1 that is thermostable.

In some embodiments, the modified FGF includes one or more modifications that reduce the number of reactive thiols (e.g., free cysteines). Examples such modifications in FGF (e.g., FGF-1) are described, for example, in U.S. Pat. Nos. 5,223,483; 5,312,911; 5,409,897; 7,790,682; 7,595,296; 7,696,171; 7,776,825; 7,659,379; 8,119,776; 8,153,770; 8,153,771; and 8,461,111; U.S. Patent Application Publication Nos. 2011/0224404 and 2013/0130983; and in Xia et al. *PloS one.* 2012; 7(11):e48210. In some embodiments, positions 16, 83 and/or 117 are mutated in FGF-1 to generate a modified FGF-1 that has a reduced number of reactive thiols.

The modified FGFs described herein are uniquely suited for application in the eye. Because modified FGFs described herein can be administered without exogenous heparin in the formulation for stability, they can be formulated and applied without heparin and thus are more able to bind to the tissue heparans. Such modified FGFs have a high affinity for tissue heparans that are exposed in a surgical, traumatic or dystrophic conditions and disease-states and so bind to diseased tissue on application. In addition, the modified FGFs being more thermally stable are suitable for formulation and storage at room temperature. The stability of the modified FGFs also makes them suitable for administration in both solution (e.g., immediate release) and sustained-release formulations.

The modified FGFs described herein are also uniquely suited for application to regeneration of tissue without conversion of the proliferating cells to fibroblasts or the induction of a fibroblastic or myofibroblastic phenotype (epi- or endo-thelilal mesenchymal transition or EMT) or scar formation. FGF-1 is known to inhibit EMT (see for example Ramos et al., Am J Physiol Lung Cell Mol Physiol 2010; 299:L222-L231). Because modified FGFs are stabilized and have longer half-lives, they can provide powerful and consistent suppression of EMT. In addition, certain eFGFs are particularly potent in suppressing the fibroblastic transition.

Modified FGFs for use in the compositions and methods described herein can be any modified FGF known in the art or described herein that is thermostable, comprises a reduced number of reactive thiols, and/or remains biologically active when administered without heparin as measured by any suitable assay known in the art or described herein.

In some embodiments, the modified FGF is any one of the modified FGF-1 proteins disclosed in U.S. Pat. Nos. 7,790, 682; 7,595,296; 7,696,171; 7,776,825; 7,659,379; 8,119, 776; 8,153,770; 8,153,771; and 8,461,111; U.S. Patent Application Publication Nos. 2011/0224404 and 2013/ 0130983; and in Xia et al. *PloS one.* 2012; 7(11):e48210. In some embodiments, the modified FGF is a wild-type FGF-1 (e.g. SEQ ID NO: 1) that has been modified at positions 12, 117, and/or 134 with, e.g., Val, Thr, Cys, Ala. In some embodiments, the amino acid positions are substituted with, e.g., Val, Ser, Thr, Cys, Ala or another amino acid to confer increased thermostability, reduce the number of reactive thiols, create disulfide linkages between modified amino acids and wild-type amino acids, or create disulfide linkages between two modified amino acids. In some embodiments, the modified FGF comprises the amino acid sequence of SEQ ID NO: 2. In some embodiments, the modified FGF is a wild-type FGF-1 (e.g. SEQ ID NO: 1) that has been modified at positions 16, 66, and/or 117 with, e.g., Val, Thr, Cys, Ala. In some embodiments, the amino acid positions are substituted with, e.g., Val, Ser, Thr, Cys, Ala or another amino acid to confer increased thermostability, reduce the number of reactive thiols, create disulfide linkages between modified amino acids and wild-type amino acids, or create disulfide linkages between two modified amino acids. In some embodiments, the modified FGF comprises the amino acid sequence of SEQ ID NO: 3. In some embodiments, the modified FGF is a wild-type FGF-1 (e.g. SEQ ID NO: 1) that has been modified at positions 12, 16, 66, 117, and/or 134 with, e.g., Val, Thr, Cys, Ala. In some embodiments, the amino acid positions are substituted with, e.g., Val, Ser, Thr, Cys, Ala or another amino acid to confer increased thermostability, reduce the number of reactive thiols, create disulfide linkages between modified amino acids and wild-type amino acids, or create disulfide linkages between two modified amino acids. In some embodiments, the modified FGF comprises the amino acid sequence of SEQ ID NO: 4.

In some embodiments, the modified FGF is human wild-type FGF protein modified at position 12 with, e.g., Val, Ser, Thr, Cys, Ala or another amino acid. In some embodiments, the modified FGF is human wild-type FGF protein with the mutation Lys12Val. In some embodiments, the modified FGF is human wild-type FGF protein modified at position 16 with, e.g., Val, Ser, Thr, Cys, Ala or another amino acid. In some embodiments, the modified FGF is human wild-type FGF protein with the mutation Pro134Val. In some embodiments, the modified FGF is human wild-type FGF protein modified at position 66 with, e.g., Val, Ser, Thr, Cys, Ala or another amino acid. In some embodiments, the modified FGF is human wild-type FGF protein with the mutation Ala66Cys. In some embodiments, the modified FGF is human wild-type FGF protein modified at position 117 with, e.g., Val, Ser, Thr, Cys, Ala or another amino acid. In some embodiments, the modified FGF is human wild-type FGF protein with the mutation Cys117Val. In some embodiments, the modified FGF is human wild-type FGF protein modified at position 134 with, e.g., Val, Ser, Thr, Cys, Ala or another amino acid. In some embodiments, the modified FGF is human wild-type FGF protein with the mutation Pro134Val. In some embodiments, the modified FGF is human wild-type FGF protein modified at one or more positions 12, 117, and 134. In some embodiments, the modified FGF is human wild-type FGF protein with the mutations Lys12Val, Cys117Val, and Pro134Val. In some embodiments, the modified FGF is human wild-type FGF protein modified at one or more positions 16, 66, and 117. In some embodiments, the modified FGF is human wild-type FGF protein with the mutations Pro134Val, Ala66Cys, and Cys117Val. In some embodiments, the modified FGF is human wild-type FGF protein modified at one or more positions 12, 16, 66, 117, and 134. In some embodiments, the modified FGF is human wild-type FGF protein with the mutations Lys12Val, Pro134Val, Ala66Cys, Cys117Val, and Pro134Val. In some embodiments, the modified FGF is a wild-type FGF-1 (e.g. SEQ ID NO: 1) that has been modified at positions 12, 16, 66, 117 and/or 134. The amino acid positions can be substituted with, e.g., Val, Ser, Thr, Cys, Ala or another amino acid to confer increased thermostability, reduce the number of reactive thiols, create disulfide linkages between modified amino acids and wild-type amino acids, or create disulfide linkages between two modified amino acids. In some embodiments, the modified FGF comprises the amino acid sequence of SEQ ID NO: 4.

In some embodiments, the modified FGF is a wild-type FGF-1 (e.g. SEQ ID NO: 1) that has been modified at position 12 with, e.g., Val, Ser, Thr, Cys, Ala or another amino acid. In some embodiments, the modified FGF that has been modified at position 12 is further modified at position 16 with, e.g., Val, Ser, Thr, Cys, Ala or another amino acid. In some embodiments, the modified FGF that has been modified at position 12 is further modified at position 66 with, e.g., Val, Ser, Thr, Cys, Ala or another amino acid. In some embodiments, the modified FGF that has been modified at position 12 is further modified at position 117 with, e.g., Val, Ser, Thr, Cys, Ala or another amino acid. In some embodiments, the modified FGF that has been modified at position 12 is further modified at position 134 with, e.g., Val, Ser, Thr, Cys, Ala or another amino acid. In some embodiments, the modified FGF that has been modified at position 12 and position 16 is further modified at position 66 with, e.g., Val, Ser, Thr, Cys, Ala or another amino acid. In some embodiments, the modified FGF that has been modified at position 12 and position 16 is further modified at position 117 with, e.g., Val, Ser, Thr, Cys, Ala or another amino acid. In some embodiments, the modified FGF that has been modified at position 12 and position 16 is further modified at position 134 with, e.g., Val, Ser, Thr, Cys, Ala or another amino acid. In some embodiments, the modified FGF that has been modified at position 12, 16 and 66 is further modified at position 117 with, e.g., Val, Ser, Thr, Cys, Ala or another amino acid. In some embodiments, the modified FGF that has been modified at position 12, 16 and 66 is further modified at position 134 with, e.g., Val, Ser, Thr, Cys, Ala or another amino acid. In some embodiments, the modified FGF that has been modified at position 12, 16, 66 and 117 is further modified at position 134 with, e.g., Val, Ser, Thr, Cys, Ala or another amino acid. In some embodiments, the modified FGF that has been modified at position 12 and position 66 is further modified at position 117 with, e.g., Val, Ser, Thr, Cys, Ala or another amino acid. In some embodiments, the modified FGF that has been modified at position 12 and position 66 is further modified at position 134 with, e.g., Val, Ser, Thr, Cys, Ala or another amino acid. In some embodiments, the modified FGF that has been modified at position 12 and position 117 is further modified at position 134 with, e.g., Val, Ser, Thr, Cys, Ala or another amino acid.

In some embodiments, the modified FGF is a wild-type FGF-1 (e.g. SEQ ID NO: 1) that has been modified at position 16 with, e.g., Val, Ser, Thr, Cys, Ala or another amino acid. In some embodiments, the modified FGF that has been modified at position 16 is further modified at position 66 with, e.g., Val, Ser, Thr, Cys, Ala or another amino acid. In some embodiments, the modified FGF that has been modified at position 16 is further modified at position 117 with, e.g., Val, Ser, Thr, Cys, Ala or another amino acid. In some embodiments, the modified FGF that has been modified at position 16 is further modified at position 134 with, e.g., Val, Ser, Thr, Cys, Ala or another amino acid. In some embodiments, the modified FGF that has been modified at position 16 and position 66 is further modified at position 117 with, e.g., Val, Ser, Thr, Cys, Ala or another amino acid. In some embodiments, the modified FGF that has been modified at position 16 and position 66 is further modified at position 134 with, e.g., Val, Ser, Thr, Cys, Ala or another amino acid. In some embodiments, the modified FGF that has been modified at position 16, 66 and 117 is further modified at position 134 with, e.g., Val, Ser, Thr, Cys, Ala or another amino acid. In some embodiments, the modified FGF that has been modified at position 16 and position 117 is further modified at position 134 with, e.g., Val, Ser, Thr, Cys, Ala or another amino acid.

In some embodiments, the modified FGF is a wild-type FGF-1 (e.g. SEQ ID NO: 1) that has been modified at position 66 with, e.g., Val, Ser, Thr, Cys, Ala or another amino acid. In some embodiments, the modified FGF that has been modified at position 66 is further modified at position 117 with, e.g., Val, Ser, Thr, Cys, Ala or another amino acid. In some embodiments, the modified FGF that has been modified at position 66 is further modified at position 134 with, e.g., Val, Ser, Thr, Cys, Ala or another amino acid. In some embodiments, the modified FGF that has been modified at position 66 and position 117 is further modified at position 134 with, e.g., Val, Ser, Thr, Cys, Ala or another amino acid.

In some embodiments, the numbering of the amino acid residues of SEQ ID NO: 1, SEQ ID NO:2, SEQ ID NO:3, and SEQ ID NO: 4 are based on the 140 amino acid numbering nomenclature for FGF-1.

In some embodiments, the modified FGF is a wild-type FGF-1 (e.g. SEQ ID NO: 1) that has been modified at position 117 with, e.g., Val, Ser, Thr, Cys, Ala or another amino acid. In some embodiments, the modified FGF that has been modified at position 117 is further modified at position 134 with, e.g., Val, Ser, Thr, Cys, Ala or another amino acid.

In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to wild-type human FGF-1. In some embodiments, the modified FGF comprises the wild-type human FGF-1 sequence with about 1, about 2, about 3, about 4, about 5, about 6, about 7, about 8, about 9, or about 10 residues deleted from the N-terminus. In some embodiments, the modified FGF comprises the wild-type human FGF-1 sequence with about 1, about 2, about 3, about 4, about 5, about 6, about 7, about 8, about 9, or about 10 residues deleted from the C-terminus. In some embodiments, the sequence of the modified FGF comprises 50%, 55%, 60%, 65%, 70%, 75%, 80%, 85%, 90%, 95%, or 100% 85%, 86%, 87%, 88%, 89%, 90%, 91%, 92%, 93%, 94%, 95%, 96%, 97%, 98%, 99% or 100% sequence identity to SEQ ID NO: 1. In some embodiments, the modified FGF comprises the sequence of SEQ ID NO: 1 with about 1, about 2, about 3, about 4, about 5, about 6, about 7, about 8, about 9, or about 10 residues deleted from the N-terminus. In some embodiments, the modified FGF comprises the sequence of SEQ ID NO: 1 with about 1, about 2, about 3, about 4, about 5, about 6, about 7, about 8, about 9, or about 10 residues deleted from the C-terminus.

In some embodiments, the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to wild-type human FGF-1 mutated at position 12 with, for example, the mutation Lys12Val. In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 12 with, for example, the mutation Lys12Val. In some embodiments, the modified FGF comprises the wild-type human FGF-1 sequence with a mutation at position 12, for example the mutation Lys12Val, and with about 1, about 2, about 3, about 4, about 5, about 6, about 7, about 8, about 9, or about 10 residues deleted from the N-terminus. In some embodiments, the modified FGF comprises the sequence of SEQ ID NO: 1 with a mutation at position 12, for example the mutation Lys12Val, and with about 1, about 2, about 3, about 4, about 5, about 6, about 7, about 8, about 9, or about 10 residues deleted from the C-terminus.

In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to wild-type human FGF-1 mutated at position 16 with, for example, the mutation Cys16Ser. In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 16 with, for example, the mutation Cys16Ser. In some embodiments, the modified FGF comprises the wild-type human FGF-1 sequence with a mutation at position 12, for example the mutation Cys16Ser, and with about 1, about 2, about 3, about 4, about 5, about 6, about 7, about 8, about 9, or about 10 residues deleted from the N-terminus. In some embodiments, the modified FGF comprises the sequence of SEQ ID NO: 1 with a mutation at position 12, for example the mutation Cys16Ser, and with about 1, about 2, about 3, about 4, about 5, about 6, about 7, about 8, about 9, or about 10 residues deleted from the C-terminus.

In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to wild-type human FGF-1 mutated at position 66 with, for example, the mutation Ala66Cys. In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 66 with, for example, the mutation Ala66Cys. In some embodiments, the modified FGF comprises the wild-type human FGF-1 sequence with a mutation at position 12, for example the mutation Ala66Cys, and with about 1, about 2, about 3, about 4, about 5, about 6, about 7, about 8, about 9, or about 10 residues deleted from the N-terminus. In some embodiments, the modified FGF comprises the sequence of SEQ ID NO: 1 with a mutation at position 12, for example the mutation Ala66Cys, and with about 1, about 2, about 3, about 4, about 5, about 6, about 7, about 8, about 9, or about 10 residues deleted from the C-terminus.

In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to wild-type human FGF-1 mutated at position 117 with, for example, the mutation Cys117Val. In some embodiments, the modified FGF comprises 50%, 55%, 60%, 65%, 70%, 75%, 80%, 85%, 90%, 95%, or 100% 85%, 86%, 87%, 88%, 89%, 90%, 91%, 92%, 93%, 94%, 95%, 96%, 97%, 98%, 99% or 100% sequence identity to SEQ ID NO: 1 mutated at position 117 with, for example, the mutation Cys117Val. In some embodiments, the modified FGF comprises the wild-type human FGF-1 sequence with a mutation at position 12, for example the mutation Cys117Val, and with about 1, about 2, about 3, about 4, about 5, about 6, about 7, about 8, about 9, or about 10 residues deleted from the N-terminus. In some embodiments, the modified FGF comprises the sequence of SEQ ID NO: 1 with a mutation at position 12, for example the mutation Cys117Val, and with about 1, about 2, about 3, about 4, about 5, about 6, about 7, about 8, about 9, or about 10 residues deleted from the C-terminus.

In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to wild-type human FGF-1 mutated at position 134 with, for example, the mutation Pro134Val. In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at position 134 with, for example, the mutation Pro134Val. In some embodiments, the modified FGF comprises the wild-type human FGF-1 sequence with a mutation at position 12, for example the mutation Pro134Val, and with about 1, about 2, about 3, about 4, about 5, about 6, about 7, about 8, about 9, or about 10 residues deleted from the N-terminus. In some embodiments, the modified FGF comprises the sequence of SEQ ID NO: 1 with a mutation at position 12, for example the mutation Pro134Val, and with about 1, about 2, about 3, about 4, about 5, about 6, about 7, about 8, about 9, or about 10 residues deleted from the C-terminus.

In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to wild-type human FGF-1 mutated at one or more positions 12, 117, and 134 with, for example, the mutations Lys12Val, Cys117Val, and Pro134Val. In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at one or more positions 12, 117, and 134 with, for example, the mutations Lys12Val, Cys117Val, and Pro134Val. In some embodiments, the modified FGF comprises the wild-type human FGF-1 sequence with a mutation at positions 12, 117 and 134, for example the mutations Lys12Val, Cys117Val, and Pro134Val, and with about 1, about 2, about 3, about 4, about 5, about 6, about 7, about 8, about 9, or about 10 residues deleted from the N-terminus. In some embodiments, the modified FGF comprises the sequence of SEQ ID NO: 1 with mutations at position 12, 117 and 134, for example the mutations Lys12Val, Cys117Val, and Pro134Val, and with about 1, about 2, about 3, about 4, about 5, about 6, about 7, about 8, about 9, or about 10 residues deleted from the C-terminus.

In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to wild-type human FGF-1 mutated at one or more positions 16, 66, and 117 with, for example, the mutations Cys16Ser, Ala66Cys, and Cys117Val. In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 mutated at one or more positions 16, 66, and 117 with, for example, the mutations Cys16Ser, Ala66Cys, and Cys117Val. In some embodiments, the modified FGF comprises the wild-type human FGF-1 sequence with a mutation at positions 16, 66 and 117, for example the mutations Cys16Ser, Ala66Cys, and Cys117Val, and with about 1, about 2, about 3, about 4, about 5, about 6, about 7, about 8, about 9, or about 10 residues deleted from the N-terminus. In some embodiments, the modified FGF comprises the sequence of SEQ ID NO: 1 with mutations at position 16, 66 and 117, for example the mutations Cys16Ser, Ala66Cys, and Cys117Val, and with about 1, about 2, about 3, about 4, about 5, about 6, about 7, about 8, about 9, or about 10 residues deleted from the C-terminus.

In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to wild-type human FGF-1 mutated at one or more positions 12, 16, 66, 117, and 134 with, for example, the mutations Lys12Val, Cys16Ser, Ala66Cys, Cys117Val, Pro134Val. In some embodiments, the sequence of the modified FGF comprises 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% sequence identity to SEQ ID NO: 1 at one or more positions 12, 16, 66, 117, and 134 with, for example, the mutations Lys12Val, Cys16Ser, Ala66Cys, Cys117Val, Pro134Val. In some embodiments, the modified FGF comprises the wild-type human FGF-1 sequence with a mutation at positions 12, 16, 66, 117, and 134 for example the mutations Lys12Val, Cys16Ser, Ala66Cys, Cys117Val, Pro134Val and with about 1, about 2, about 3, about 4, about 5, about 6, about 7, about 8, about 9, or about 10 residues deleted from the N-terminus. In some embodiments, the modified FGF comprises the sequence of SEQ ID NO: 1 with mutations at position 12, 16, 66, 117, and 134 for example the mutations Lys12Val, Cys16Ser, Ala66Cys, Cys117Val, Pro134Val, and with about 1, about 2, about 3, about 4, about 5, about 6, about 7, about 8, about 9, or about 10 residues deleted from the C-terminus.

In some embodiments, the signal peptide is removed from the modified FGF. In some embodiments, the signal peptide is not removed from the modified FGF.

In some embodiments, the modified FGFs or compositions described herein may be prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug.

The modified FGFs described herein may be labeled isotopically (e.g. with a radioisotope) or by other means, including, but not limited to, the use of chromophores or fluorescent moieties, bioluminescent labels, photoactivatable or chemiluminescent labels.

In some embodiments, the synthesis of modified FGFFs described herein is accomplished using means described in the art, using the methods described herein, or by a combination thereof.

Sequences
SEQ ID NO: 1 is as follows:

FNLPPGNYKKPKLLYCSNGGHFLRILPDGTVDGTRDRSDQHIQLQLSAES
VGEVYIKSTETGQYLAMDTDGLLYGSQTPNEECLFLERLEENHYNTYISK
KHAEKNWFVGLKKNGSCKRGPRTHYGQKAILFLPLPVSSD

SEQ ID NO: 2 is as follows:

FNLPPGNYKKPVLLYCSNGGHFLRILPDGTVDGTRDRSDQHIQLQLSAES
VGEVYIKSTETGQYLAMDTDGLLYGSQTPNEECLFLERLEENHYNTYISK
KHAEKNWFVGLKKNGSVKRGPRTHYGQKAILFLVLPVSSD

SEQ ID NO: 3 is as follows:

FNLPPGNYKKPKLLYSSNGGHFLRILPDGTVDGTRDRSDQHIQLQLSAES
VGEVYIKSTETGQYLCMDTDGLLYGSQTPNEECLFLERLEENHYNTYISK
KHAEKNWFVGLKKNGSVKRGPRTHYGQKAILFLPLPVSSD

SEQ ID NO: 4 is as follows:

FNLPPGNYKKPVLLYSSNGGHFLRILPDGTVDGTRDRSDQHIQLQLSAES
VGEVYIKSTETGQYLCMDTDGLLYGSQTPNEECLFLERLEENHYNTYISK
KHAEKNWFVGLKKNGSVKRGPRTHYGQKAILFLVLPVSSD

Methods of Use

Provided herein is a method of treating an ocular disease, disorder or condition in a mammal comprising administering to the mammal a modified fibroblast growth factor (FGF).

In some embodiments, the ocular disease, disorder or condition to be treated is a disease, disorder, or condition of the corneal endothelial layer. Diseases, disorders, or conditions of the corneal endothelial layer include, but are not limited to, Fuch's dystrophy, bullous keratopathy, congenital hereditary endothelial dystrophy 1, congenital hereditary endothelial dystrophy 2, posterior polymorphous corneal dystrophy, and dry eye syndromes.

Without being bound by theory, it is believed a solution of a modified FGF injected intracamerally into the aqueous humor of the eye binds to the endothelial surface and especially any areas of the cornea that are not covered by a healthy endothelial layer. The modified FGF stimulates the growth and migration of the endothelial cells. This reduces the corneal edema associated with the endothelial dystrophy and reduces the likelihood for a need for a corneal or endothelial transplant. The action of the modified FGF can occur at a site other than the site of greatest dystrophy (typically at the corneal center) and also results in stimulation of endothelial cells in the corneal periphery and endothelial progenitor pools in the trabecular meshwork (TM).

In some embodiments, the ocular disease, disorder or condition to be treated is a disease, disorder, or condition of the corneal epithelium. Diseases, disorders or conditions of the corneal epithelium include, but are not limited to, dry eye syndromes, inflammatory conditions such as Stevens-Johnson syndrome, and corneal epithelial defects.

In further embodiments, the modified FGFs described herein can be used to treat epithelial basement membrane dystrophy, Meesmann juvenile epithelial corneal dystrophy, gelatinous drop-like corneal dystrophy, Lisch epithelial corneal dystrophy, subepithelial mucinous corneal dystrophy, Reis-Bucklers corneal dystrophy, or Thiel-Behnke dystrophy, and recurrent corneal erosions.

In some embodiments, the ocular condition includes damage to the cornea (e.g., the corneal surface or endothelial layer at the interface of the cornea and aqueous humor) or surgical disruption caused by corneal surgeries, including PRK, LASIK, and any penetrating corneal surgery or keratoplasty.

In some embodiments, the ocular condition includes accidental trauma or chemical or thermal injury to the cornea. In some embodiments, the ocular condition comprises mustard gas keratopathy.

In some embodiments, the ocular disease, disorder or condition to be treated is a disease, disorder, or condition of the corneal stroma. Diseases, disorders or conditions of the corneal stroma include, but are not limited to, keratoconus, lattice corneal dystrophy, granular corneal dystrophy, macular corneal dystrophy, Schnyder crystalline corneal dystrophy, congenital stromal corneal dystrophy, fleck corneal dystrophy, trauma or chemical or thermal injury, or injury secondary to infections such as trachoma.

In further embodiments, the modified FGFs described herein can be applied before, during, or after corneal transplantations procedures (e.g., corneal transplantation or procedures involving Descemet's membrane) that involve disruption of the cornea (e.g., corneal endothelial structure) where acceleration of healing of corneal or ocular surface cells and/or improving the cellular response (e.g, by increasing the viability and/or longevity of the transplanted cells) to insult would result in a therapeutic benefit.

In additional embodiments, the modified FGFs described herein can be used to increase the viability and health of corneal cells or corneal progenitors being prepared for transplantation. Modified FGFs added to the organ culture medium for donated corneas or other donated corneal tissue stimulates the corneal cells and increases the length of time the corneas can be stored before transplantation, as well as increasing the probability that a cornea will have sufficient healthy cells to be useful for transplantation. Also, the modified FGFs can be used in culture media when culturing corneal progenitor cells to stimulate growth of those cells.

Further embodiments relate to methods of modulating the activity of one or more fibroblast growth factor receptors (FGFRs) in a corneal endothelial cell comprising contacting said corneal endothelial cell with a modified FGF (e.g., a modified FGF-1, such as one comprising the sequence of SEQ ID NO: 2, SEQ ID NO: 3, SEQ ID NO: 4, or a combination thereof). Such methods can be used to increase or stimulate the activity of one or more FGFRs, which can result in increased cell migration and/or cell proliferation.

In some embodiments one or more modified FGFs (e.g., a modified FGF having the sequence of SEQ ID NO: 2, a modified FGF having the sequence of SEQ ID NO: 3, or a modified FGF having the sequence of SEQ ID NO: 4) are used to induce regeneration or tissue healing without EMT or scarring. In some embodiments, modified FGFs described herein FGFs (e.g. a modified FGF having the sequence of SEQ ID NO: 2, a modified FGF having the sequence of SEQ ID NO: 3, or a modified FGF having the sequence of SEQ ID NO: 4) are used to decrease the amount of scarring associated with the healing process. In some embodiments, modified FGFs (e.g. a modified FGF having the sequence of SEQ ID NO: 2, a modified FGF having the sequence of SEQ ID NO: 3, or a modified FGF having the sequence of SEQ ID NO: 4) are applied to surgical incisions to reduce the amount of scar formation. This is particularly useful where the scarring response results in decreased function of the tissue, for example in trabeculectomy procedures where scarring of the tissue leads to blockage of the drainage channel created by the trabeculectomy. This is also useful where scar tissue formation is esthetically undesirable, such as in surgical incisions to the skin.

Pharmaceutical Compositions, Methods of Administration, and Dosing

Pharmaceutical compositions comprising a modified FGF described herein may be formulated in a conventional manner using one or more physiologically acceptable carriers including excipients and auxiliaries which facilitate processing of the active compounds into preparations which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a modified FGF with other chemical components, such as carriers, stabilizers, diluents, dispersing agents, suspending agents, thickening agents, and/or excipients, and, optionally, other therapeutic and/or prophylactic ingredients. The pharmaceutical composition facilitates administration of the modified FGF to an organism. In practicing the methods of treatment or use provided herein, therapeutically effective amounts of modified FGFs described herein are administered in a pharmaceutical composition to a mammal having an ocular disease, disorder, or condition to be treated. In some embodiments, the mammal is a human. A therapeutically effective amount can vary widely depending on the severity of the disease, the age and relative health of the subject, the potency of the compound used and other factors. A pharmaceutically acceptable or suitable composition includes an ophthalmologically suitable or acceptable composition.

A pharmaceutical composition (e.g., for delivery by injection or for application as an eye drop) may be in the form of a liquid or solid. A liquid pharmaceutical composition may include, for example, one or more of the following: sterile diluents such as water for injection, saline solution, preferably physiological saline, Ringer's solution, isotonic sodium chloride, phosphate-buffer saline, citrate-buffer saline, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. Physiological saline is commonly used as an excipient, and an injectable pharmaceutical composition or a composition that is delivered ocularly is preferably sterile.

A modified FGF or pharmaceutical composition described herein can be delivered to a subject by any suitable means, including, for example, topically, intraocularly, intracamerally, orally, parenterally, intravenously, intraperitoneally, intranasally (or other delivery methods to the mucous membranes, for example, of the nose, throat, and bronchial tubes), or by local administration to the eye, or by an intraocular or periocular device. Modes of local administration can include, for example, topical application, eye drops, intraocular injection or periocular injection. Periocular injection typically involves injection of the compound under the conjunctiva or into the Tennon's space (beneath the fibrous tissue overlying the eye). Intraocular injection typically involves injection of the modified FGF or pharmaceutical composition into the vitreous human or aqueous humor. In certain embodiments, the administration is non-invasive, such as by topical application or eye drops.

A modified FGF or pharmaceutical composition described herein can be formulated for administration using pharmaceutically acceptable (suitable) carriers or vehicles as well as techniques routinely used in the art. A pharmaceutically acceptable or suitable carrier includes an ophthalmologically suitable or acceptable carrier. A carrier is selected according to the solubility of the particular modified FGF. Suitable ophthalmological compositions and formulations include those that are administrable locally to the eye, such as by eye drops, injection or the like. In the case of eye drops, the formulation can also optionally include, for example, ophthalmologically compatible agents such as isotonizing agents such as sodium chloride, concentrated glycerin, and the like; buffering agents such as sodium phosphate, sodium acetate, and the like; surfactants such as polyoxyethylene sorbitan mono-oleate (also referred to as Polysorbate 80), polyoxyl stearate 40, polyoxyethylene hydrogenated castor oil, and the like; stabilization agents such as sodium citrate, sodium edentate, and the like; preservatives such as benzalkonium chloride, parabens, and the like; and other ingredients. Preservatives can be employed, for example, at a level of from about 0.001 to about 1.0% weight/volume. The pH of the formulation is usually within the range acceptable to ophthalmologic formulations, such as within the range of about pH 4 to 8.

For injection, the modified FGF or pharmaceutical composition can be provided in an injection grade saline solution, in the form of an injectable liposome solution, slow-release polymer system or the like. Intraocular and periocular injections are known to those skilled in the art and are described in numerous publications including, for example, Spaeth, Ed., *Ophthalmic Surgery: Principles of Practice*, W. B. Sanders Co., Philadelphia, Pa., 85-87, 1990.

In some embodiments, the modified FGF or pharmaceutical composition (e.g., an ophthalmic formulation) is administered via microneedles into the cornea (Jiang et al. (2007). *Invest Ophthalmol Vis Sci* 48(9): 4038-4043). A microneedle array is coated with the modified FGF or pharmaceutical composition and pressed against the cornea such that the microneedles penetrate into the corneal stroma but do not penetrate the entire cornea. It is then removed, and the modified FGF or pharmaceutical composition is left behind in the corneal stroma. This modified FGF or pharmaceutical composition can stimulates the corneal cells to proliferate and migrate, and suppresses the scarring response that the stromal cells normally have.

For delivery of a composition comprising at least one of the modified FGFs described herein via a mucosal route, which includes delivery to the nasal passages, throat, and airways, the composition may be delivered in the form of an aerosol. The compound may be in a liquid or powder form for intramucosal delivery. For example, the composition may be delivered via a pressurized aerosol container with a suitable propellant, such as a hydrocarbon propellant (e.g., propane, butane, isobutene). The composition may be delivered via a non-pressurized delivery system such as a nebulizer or atomizer.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The modified FGFs or pharmaceutical compositions described herein may be formulated for sustained or slow-release. Such compositions may generally be prepared using well known technology and administered by, for example, periocular, intraocular, rectal, oral or subcutaneous implantation, or by implantation at the desired target site, or by topical application. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained-release formulation depends upon the site of implantation, the rate and expected duration of release, and the nature of the condition to be treated or prevented.

Systemic drug absorption of a drug or composition administered via an ocular route is known to those skilled in the art (see, e.g., Lee et al., *Int. J. Pharm.* 233:1-18 (2002)). In one embodiment, a compound described herein is delivered by a topical ocular delivery method (see, e.g., *Curr. Drug Metab.* 4:213-22 (2003)). The composition may be in the form of an eye drop, salve, or ointment or the like, such as, aqueous eye drops, aqueous ophthalmic suspensions, non-aqueous eye drops, and non-aqueous ophthalmic suspensions, gels, ophthalmic ointments, etc. For preparing a gel, for example, carboxyvinyl polymer, methyl cellulose, sodium alginate, hydroxypropyl cellulose, ethylene maleic anhydride polymer and the like can be used.

In another embodiment, the modified FGF solution or pharmaceutical composition (e.g., an ophthalmic formulation) contains hyaluronic acid, carboxymethyl cellulose, or other polysaccharides that provide increased ocular tolerability, viscosity and osmolality to produce a comfortable ocular solution.

The dose of the modified FGF or pharmaceutical composition comprising at least one of the modified FGFs described herein may differ, depending upon the patient's (e.g., human) condition, that is, stage of the ocular disease, disorder, or condition, general health status, age, and other factors that a person skilled in the medical art will use to determine dose. When the composition is used as eye drops, for example, one to several drops per unit dose, preferably 1 or 2 drops (about 50 µl per 1 drop), may be applied about 1 to about 6 times daily.

Pharmaceutical compositions may be administered in a manner appropriate to the ocular disease, disorder, or condition to be treated (or prevented) as determined by persons skilled in the medical arts. An appropriate dose and a suitable duration and frequency of administration will be determined by such factors as the condition of the patient, the type and severity of the patient's disease, disorder, or condition, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free, or a lessening of symptom severity). For prophylactic use, a dose should be sufficient to prevent, delay the onset of, or diminish the severity of an ocular disease, disorder, or condition. Optimal doses may generally be determined using experimental models and/or clinical trials. The optimal dose may depend upon the body mass, weight, or blood volume of the patient.

The doses of the modified FGFs or pharmaceutical compositions can be suitably selected depending on the clinical status, condition and age of the subject, dosage form and the like. In the case of eye drops, a modified FGF described herein can be administered, for example, from about 1 pg/ml to about 100 mg/ml from about 1 ng/ml to about 100 mg/ml of the modified FGF one to seven times per week. In the case of intracameral injection, a modified FGF described herein can be administered about once per month, about once every two months, about once every three months, about once every four months, about once every five months, about once every six months, about once every seven months, about once every eight months, about once every nine months, about once every ten months, about once every eleven months, or about once every twelve months. In the case of topical administration, a modified FGF described herein can be administered, about once per day, about twice per day, about three times per day, about once every other day, about once every three days, about once every four days, about once every five days, about once every six days, or about once per week.

Also provided are methods of manufacturing the modified FGFs and pharmaceutical compositions described herein. A composition comprising a pharmaceutically acceptable excipient or carrier and at least one of the modified FGFs described herein may be prepared by synthesizing the modified FGF according to any one of the methods described herein or practiced in the art and then formulating the compound with a pharmaceutically acceptable carrier. Formulation of the composition will be appropriate and dependent on several factors, including but not limited to, the delivery route, dose, and stability of the compound.

At least one modified FGF described herein can be administered to human or other nonhuman vertebrates. In certain embodiments, the modified FGF is substantially pure, in that it contains less than about 5% or less than about 1%, or less than about 0.1%, of other organic molecules, such as contaminating intermediates or by-products that are created, for example, in one or more of the steps of a synthesis method. In other embodiments, a combination of one or more modified FGFs described herein can be administered.

The compositions described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions described herein are administered to a patient susceptible to or otherwise at risk of a particular disease, disorder or condition.

Such an amount is defined to be a "prophylactically effective amount or dose." In this use, the precise amounts also depend on the patient's state of health, weight, and the like.

In the case wherein the patient's condition does not improve, upon the doctor's discretion the administration of the compositions may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compositions may be given continuously; alternatively, the dose of drug being administered may be temporarily reduced or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more modified FGFs. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Treatments

The modified FGFs and pharmaceutical compositions may also be used in combination with other therapeutic agents that are selected for their therapeutic value for the condition to be treated. Such agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

The particular choice of these optional additional agents used will depend upon the diagnosis of the attending physicians and their judgment of the condition of the patient and the appropriate treatment protocol. The agents may be administered concurrently (e.g., simultaneously, essentially simultaneously or within the same treatment protocol) or sequentially, depending upon the nature of the disease, disorder, or condition, the condition of the patient, and the actual choice of agents used. The determination of the order of administration, and the number of repetitions of administration of each therapeutic agent during a treatment protocol, is well within the knowledge of the physician after evaluation of the disease being treated and the condition of the patient.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For example, the modified FGF-1 may be incorporated into formulations that contain other active ingredients such as steroids, antibiotics, anti-inflammatories, cytokines such as IL-1 or analogs of IL-1, or antagonists of cytokines such as inhibitors of IL-17.

Other exemplary cytokines include, but are not limited to, interleukins (e.g., IL-2, IL-3, IL-4, IL-5, IL-6, IL-7, IL-8, IL-9, IL-10, IL-11, IL-12, IL-13, IL-14 IL-15, IL-16, IL-17, IL-18, IL-1α, IL-1β, and IL-1 RA), granulocyte colony stimulating factor (G-CSF), granulocyte-macrophage colony stimulating factor (GM-CSF), oncostatin M, erythropoietin, leukemia inhibitory factor (LIF), interferons, B7.1 (also known as CD80), B7.2 (also known as B70, CD86), TNF family members (TNF-α, TNF-β, LT-β, CD40 ligand, Fas ligand, CD27 ligand, CD30 ligand, 4-1BBL, Trail), and migration inhibitory factor MIF.

In some embodiments, combinations or pharmaceutical compositions described herein are administered in immunosuppressive therapy to reduce, inhibit, or prevent activity of the immune system. Immunosuppressive therapy is clinically used to: prevent the rejection of transplanted organs and tissues; treatment of autoimmune diseases or diseases that are most likely of autoimmune origin; and treatment of some other non-autoimmune inflammatory diseases.

In some embodiments, the modified FGFs and pharmaceutical compositions described herein are administered with one or more anti-inflammatory agent including, but not limited to, non-steroidal anti-inflammatory drugs (NSAIDs) and corticosteroids (glucocorticoids).

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, and COX-2 specific inhibitors (such as, but not limited to, celecoxib, rofecoxib, valdecoxib, parecoxib, etoricoxib, lumiracoxib, CS-502, JTE-522, L-745,337 and NS398).

Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

Other agents used as anti-inflammatories include those disclosed in U.S. patent publication 2005/0227929, herein incorporated by reference.

Some commercially available anti-inflammatories include, but are not limited to: Arthrotec® (diclofenac and misoprostol), Asacol®(5-aminosalicyclic acid), Salofalk® (5-aminosalicyclic acid), Auralgan® (antipyrine and benzocaine), Azulfidine® (sulfasalazine), Daypro® (oxaprozin), Lodine®(etodolac), Ponstan®(mefenamic acid), Solumedrol® (methylprednisolone), Bayer®(aspirin), Bufferin® (aspirin), Indocin® (indomethacin), Vioxx® (rofecoxib), Celebrex® (celecoxib), Bextra® (valdecoxib), Arcoxia® (etoricoxib), Prexige® (lumiracoxib), Advil®, Motrin® (ibuprofen), Voltaren®(diclofenac), Orudis®(ketoprofen), Mobic®(meloxicam), Relafen® (nabumetone), Aleve®, Naprosyn® (naproxen), Feldene® (piroxicam).

In one embodiment, compositions described herein are administered with leukotriene receptor antagonists including, but are not limited to, BAY u9773 (see EP 00791576; published 27 Aug. 1997), DUO-LT (Tsuji et al, Org. Biomol. Chem., 1, 3139-3141, 2003), zafirlukast (Accolate®), montelukast (Singulair®), prankulast (Onon®), and derivatives or analogs thereof.

In some embodiments, the modified FGFs and pharmaceutical compositions described herein are administered with one or more Rho kinase inhibitors. In some embodiments, the modified FGFs and pharmaceutical compositions described herein are administered with one or more additional growth factors, including, but not limited to epidermal growth factor (EGF) and nerve growth factor (NGF) (See, e.g., see Joyce et al. *Invest Ophthalmol. Vis Sci.* 2009; 50:2116-2122), vascular endothelial growth factor (VEGF), transforming growth factor alpha and beta (TGF-alpha and TFG-beta), platelet-derived endothelial growth factor (PD-ECGF), platelet-derived growth factor (PDGF), tumor necrosis factor alpha (TNF-alpha), hepatocyte growth factor (HGF), insulin like growth factor (IGF), erythropoietin, colony stimulating factor (CSF), macrophage-CSF (M-CSF), granulocyte/macrophage CSF (GM-CSF) and nitric oxide synthase (NOS).

Kits/Articles of Manufacture

For use in the therapeutic applications described herein, kits and articles of manufacture are also provided herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products include, e.g., U.S. Pat. Nos. 5,323, 907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of ophthalmic formulations of the modified FGFs and pharmaceutical compositions provided herein are contemplated as are a variety of treatments for any ocular disease, disorder, or condition that would benefit by administration of a modified FGF ore pharmaceutical composition described herein.

For example, the container(s) can include a modified FGF such as a modified FGF-1 having a sequence of SEQ ID NO: 2, SEQ ID NO: 3, SEQ ID NO: 4, or a combination thereof. The container(s) optionally have a sterile access port. Such kits optionally comprising compounds with an identifying descriptions or labels or instructions relating to their use in the methods described herein.

A kit will typically include one or more additional containers, each with one or more of various materials (such as reagents, optionally in concentrated form, and/or devices) desirable from a commercial and user standpoint for use of a modified FGF described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, a modified FGF pharmaceutical composition can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a modified FGF provided herein formulated in a compatible pharmaceutical carrier can also be prepared, placed in an appropriate container, and labeled for treatment of an indicated condition.

EXAMPLES

These examples are provided for illustrative purposes only and not to limit the scope of the claims provided herein. The starting materials and reagents used in the examples described herein may be synthesized or can be obtained from commercial sources.

Example 1

Effects of Modified FGF-1 on Human Corneal Endothelial Cell (HCEC) Proliferation The study was directed toward modified FGF-1 proteins having the sequence of SEQ ID NO: 2 (M1), SEQ ID NO: 3 (C3) and SEQ ID NO: 4 (C2V3). The modified FGF-1 proteins were generated using similar methods as described in Example 4.

Methods

Primary cultures of HCECs were thawed and expanded in a FNC-coated T75 flask in growth media (OptiMEM with 8% fetal bovine serum (FBS), insulin/transferrin/selenium, 20 µg/ml ascorbic acid, 200 µg/ml calcium chloride, and antibiotic/antimycotic) supplemented with 10 ng/ml FGF-1 having the sequence of SEQ ID NO: 1 (wtFGF-1).

For the proliferation assay, HCEC cells were passaged using accutase, harvested by centrifugation (200 g×12 min), resuspended in growth media without FGF and plated into FNC-coated 24-well plates (3 plates) at a seeding of 25,000 cells per well in 0.5 ml of growth medium.

At 24 hr post plating, the media was removed and replaced with base media (OptiMEM with 0.4% fetal bovine serum (FBS), insulin/transferrin/selenium, 20 µg/ml ascorbic acid, 200 mg/ml calcium chloride, and antibiotic/antimycotic) with indicated additions. For each plate, the conditions for the negative control were media with no additional FBS and the conditions for the positive control were media with a high concentration of FBS. Each modified FGF-1 protein was diluted to 1 ng/uL in base media as a stock solution and then used to generate the cell media at the tested protein concentrations of 0.3 ng/ml, 1.0 ng/ml, 3 ng/ml, and 10 ng/ml. All controls and mutant proteins were tested in quadruplicate.

Cell numbers were counted manually as the number of cells in a 20× field. The same area of the plate was counted each time, with location marked at day 1 using an ink dot on the bottom surface of the plate.

In this example, both C3 and C2V3 comprised an N-terminal his tag, which was used to purify each protein.

Results

Figure 4:
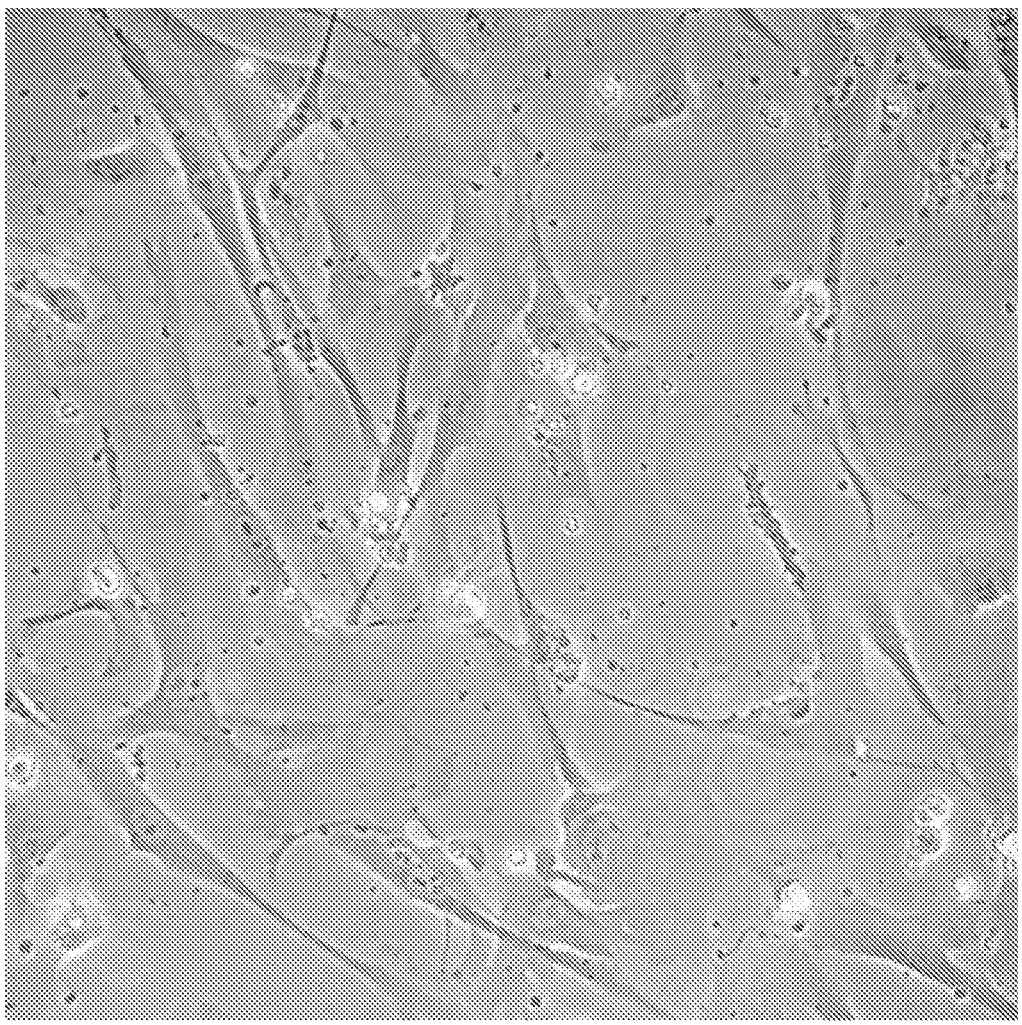
FIG. 4 depicts, as a non-limiting example, a microscopic image of HCEC cells.

The adhesion and regular distribution of the cells was checked 24 hours post plating. The cell counts per 20× field for the plates were 49±11, 53±14, and 41±8. As a non-limiting example, a microscopic image of the cells is depicted in FIG. 4, indicates the cells were fibroblastic.

Figure 5:
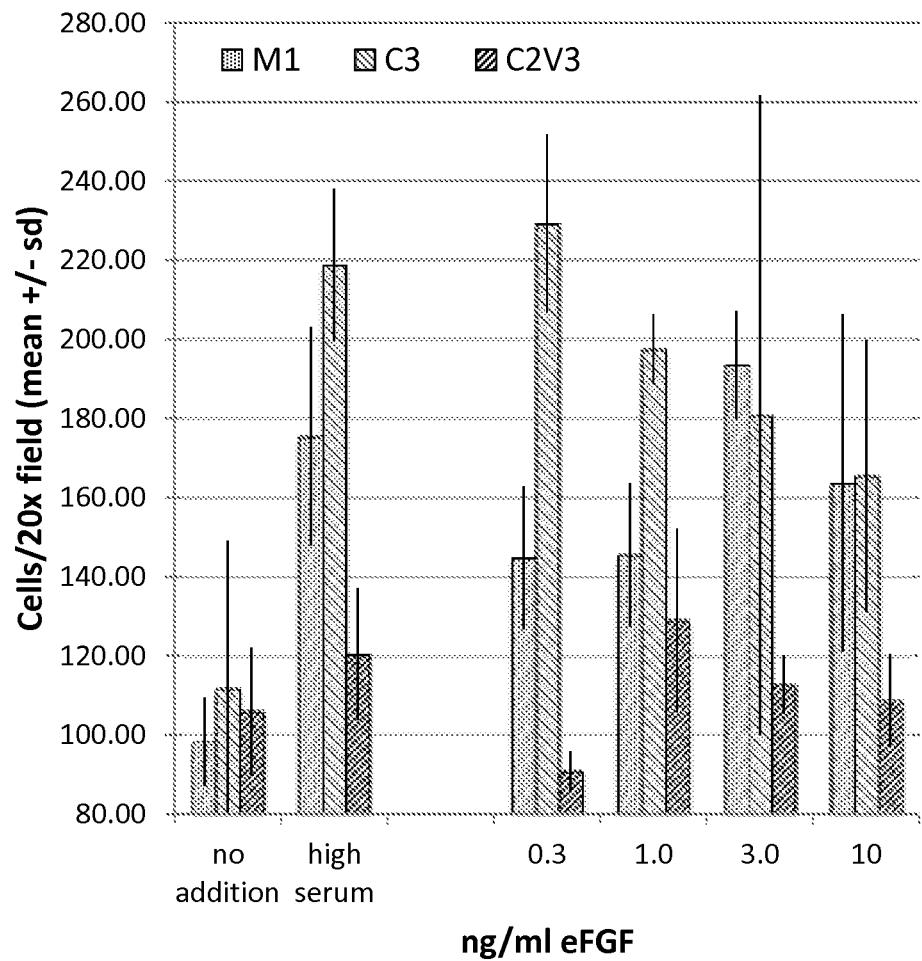
FIG. 5 depicts, as a non-limiting example, results from a human HCEC proliferation assay.

Results from cell counts at day 3 are shown, as a non-limiting example, in FIG. 5. The number of cells in the negative control in each plate approximately doubled over the three days of culture. The positive control on plate #3, which tested C2V3, was not statistically different from the negative control at the 3 day time point.

Figure 6:
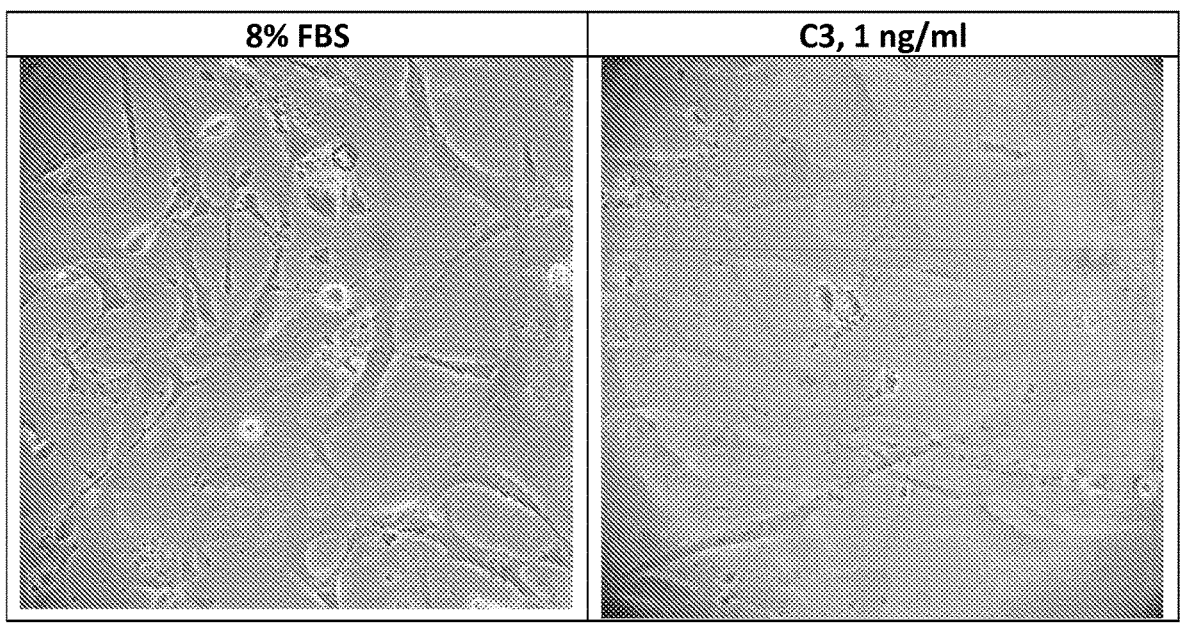
FIG. 6 depicts, as a non-limiting example, results from a human HCEC proliferation assay.

These experiments show that M1 stimulates the HCEC to grow with a dose-response similar to the previous experiment and consistent with an EC50 of about 3 ng/ml. C3 appears to stimulate maximally at the lowest dose with a reverse dose-response curve. Examination of the plate containing C3 suggests C3 has a morphological effect on the cells; cells treated with C3 appear flatter and less fibroblast-like, as can be seen in a non-limiting example depicted in FIG. 6. Overall the data show that M1 and C3 each have a mitogenic effect that resulted in cell proliferation.

Figure 7:
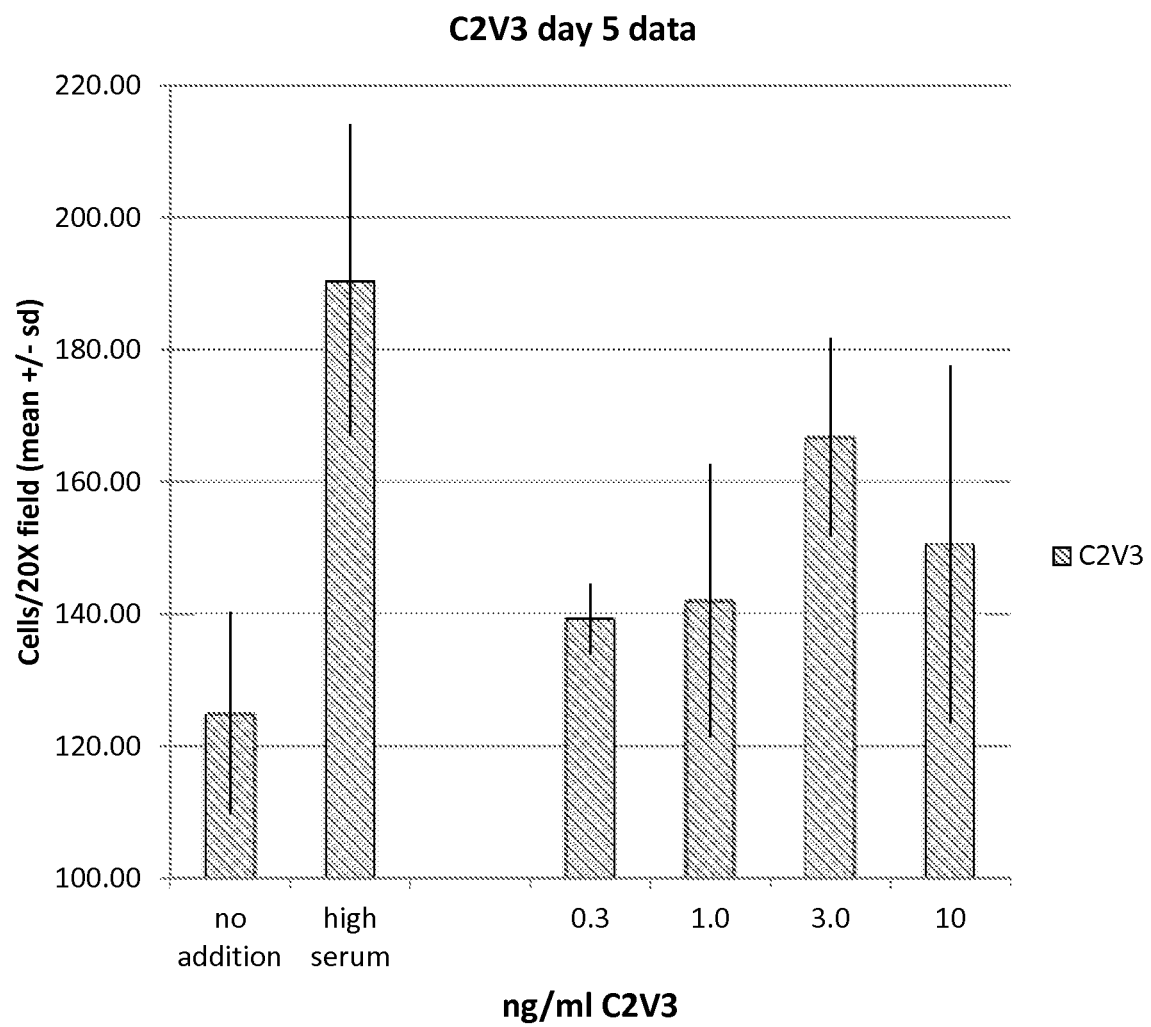
FIG. 7 depicts, as a non-limiting example, results from a human HCEC proliferation assay.

Cells were fed with media at day 3 and at day 5 after which plate 3 and cells treated with C2V3 were recounted. As shown in a non-limiting example in FIG. 7, at day 5, the positive control was statistically different from the negative control, making the plate assessment valid. In addition, the 3 ng/ml group was statistically significantly different from control indicating that C2V3 had a mitogenic effect that resulted in cell proliferation.

Discussion

Previous results using M1 were replicated and are consistent with an $EC_{50}$ of 3 ng/ml for stimulation of cell proliferation in these cells.

C3 appeared to potently stimulate the HCECs. The inverse dose response curve suggested that the peak of the effect may be at lower concentrations. Notably, this data suggested that the $EC_{50}$ of this mutant was at least 10-fold lower than the wild type FGF or other tested modified FGF-1 proteins. The morphological effect suggested that C3 may reverse the epithelial-mesenchymal transition (EMT) of these cells. This example also showed C2V3 stimulated proliferation of the HCECs. These experiments suggested that C2V3 was not more potent than wtFGF or M1.

Example 2

Effects of Modified FGF-1 on Rabbit Corneal Endothelial Cell Proliferation

The study was directed toward the modified FGF-1 protein having the sequence of SEQ ID NO: 2 (M1).

Figure 8:
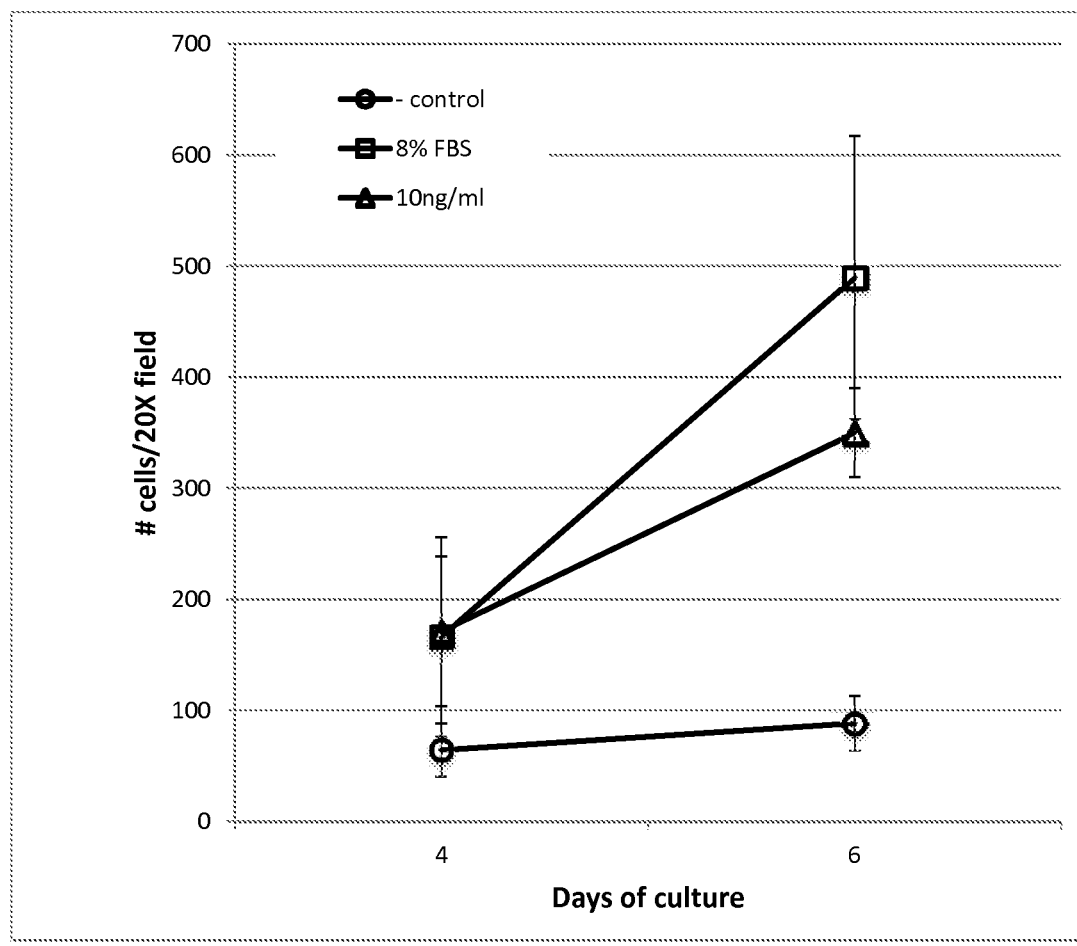
FIG. 8 depicts, as a non-limiting example, results from a rabbit CEC proliferation assay.

Primary cultures (passage 1) of rabbit corneal endothelial cells were seeded onto 12 well plates in the presence of M1 (10 ng/ml), fetal bovine serum (8% FBS) as a positive control, or no addition of fetal bovine serum as a negative control (− control). Cell numbers were counted under phase contrast for each of 3 wells per treatment. The data shows are the mean+/−sd. A pairwise comparison of the 10 ng/ml and FBS groups to control (no serum) at day 6 showed a p-value<0.05. This experiment was done in the absence of heparin. As shown in a non-limiting example in FIG. 8, M1 stimulated rabbit corneal endothelial cell proliferation.

Example 3

Effects of Modified FGF-1 on Human Corneal Endothelial Cell Proliferation

The study was directed toward the modified FGF-1 protein having the sequence of SEQ ID NO: 2. (M1)

Figure 9:
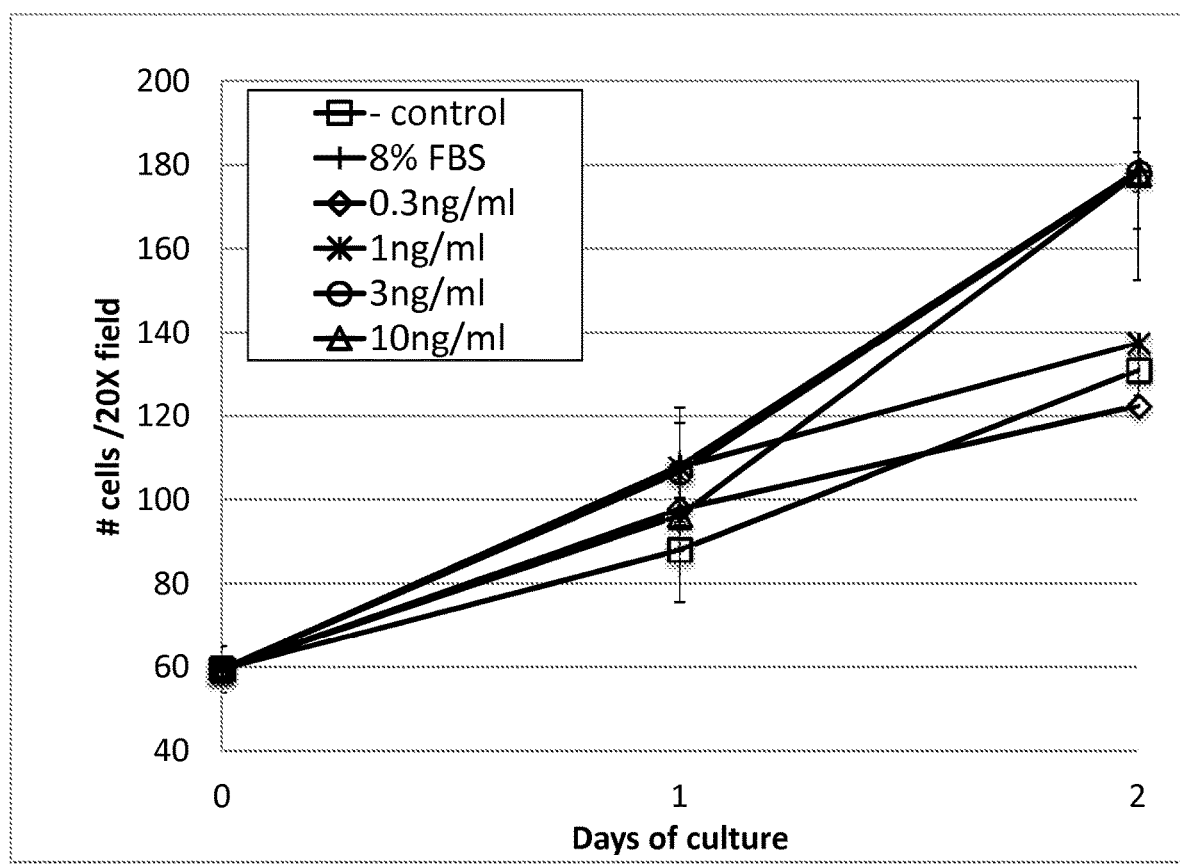
FIG. 9 depicts, as a non-limiting example, results from a human HCEC proliferation assay.

Primary cultures (passage 1) of human corneal endothelial cells from a healthy donor were seeded onto 24 well plates in the presence of fetal bovine serum (FBS, 8%) and 24 hours later treated with the indicated concentrations of M1 in media with low (0.8%) FBS. Cell numbers were counted under phase contrast for each of 4 wells per treatment. Data is mean+/−sd; pairwise comparison of the 10 ng/ml and 3 ng/ml groups to control (low serum without FGF) at day 2 p<0.05. The 8% FBS group serves as positive control. This experiment was performed in the absence of heparin. As can be seen as a non-limiting example in FIG. 9, M1 stimulated human corneal epithelial cell proliferation and was dose responsive therein.

The examples and embodiments described herein are for illustrative purposes only and in some embodiments, various modifications or changes are to be included within the purview of disclosure and scope of the appended claims.

Example 4

Production, Characterization and Biological Activity of Modified FGF-1 Peptides

The study was directed toward modified FGF-1 proteins having the sequence of SEQ ID NO: 2 (M1), SEQ ID NO: 3 (C3) and SEQ ID NO: 4 (C2V3).

Protein Purification and Oxidization

Shuffle T7 Competent *E. coli* (H3026) from New England Biolabs was used to produce C3 and C2V3. This engineered K12 *E. coli* strain provides oxidative intracellular environment for disulfide formation. C3 and C2V3 were expressed from pET21a(+)/BL21(DE3) *E. coli*. After induction with 1 mM Isopropyl-β-D-thio-galactoside (IPTG), the incubation temperature was decreased from 37° C. to 16° C. for overnight expression. The expressed protein was purified utilizing sequential column chromatography on Ni-NTA affinity resin (Qiagen, Valencia Calif.) and heparin Sepharose resin (GE Life Sciences, Pittsburgh Pa.). DTNB assay were performed on C3 and C2V3 after purification. The results showed that C3 was close to 100% oxidized, and C2V3 was about 40% oxidized. C2V3 was air oxidized in crystal buffer (no DTT, no EDTA) for 16 days at room temperature, and the DTNB assay showed more than 85% of the protein was oxidized. For C3, a non-reduced SDS-PAGE gel showed a single band which corresponded to oxidized form, and a reduced SDS-PAGE gel showed a double band which corresponded to a mixture of oxidized and reduced form. For C2V3, a non-reduced and reduced SDS-PAGE gel gel both showed a double band which indicated a mixture of oxidized and reduced form.

Isothermal Denaturation Study with Fluorescence Photospectroscopy

Figure 1B:
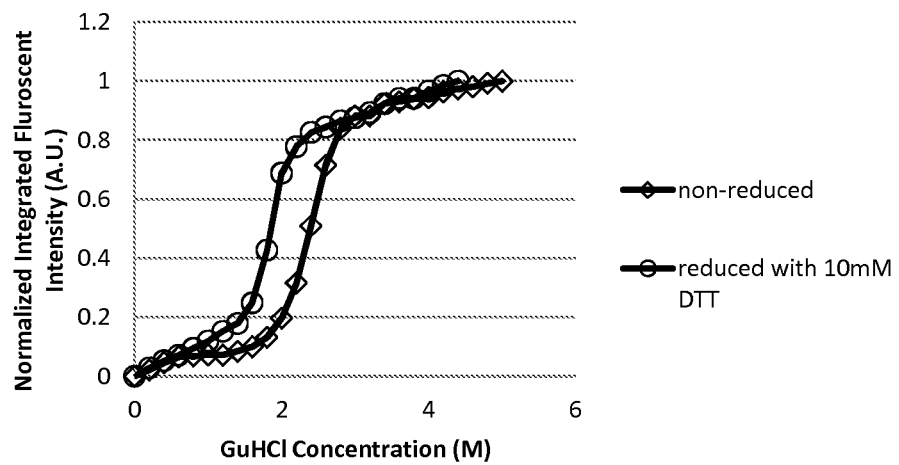
FIG. 1B depicts, as a non-limiting example, an isothermal denaturation curve of a modified FGF-1 protein with the sequence of SEQ ID NO: 4.

Each of C3 and C2V3 comprised a N-terminal his tag and was equilibrated overnight in 50 mM Na phosphate, 100 mM NaCl, with and without 10 mM DTT, pH 7.5 at 298K in 0.2 M increments of GuHCl with a final protein concentration of 5 µM. Prior to equilibration C3 was not subjected to air oxidization but C2V3 was subjected to air oxidation. Fluorescence scans were integrated to quantify the total fluorescence as a function of denaturant concentration. Data were analyzed using a six parameter two-state model. As a non-limiting example, the isothermal denaturation curve for C3, with and without 10 mM DTT, is depicted in FIG. 1A. The Cm for the non-reduced protein sample was higher than the reduced protein sample. However, both reduced and non-reduced proteins were destabilized when comparing the ΔG values. As a non-limiting example, the isothermal denaturation curve C2V3, with and without 10 mM DTT, is depicted in FIG. 1B. The Cm for the non-reduced protein sample was about 0.5M GuHCl higher than the reduced protein sample. However, the reduced form had more cooperative unfolding and had a greater ΔG value at 0 molar GuHCl. The thermodynamic parameters derived from the study are shown in Table 1.

TABLE 1

| Protein | ΔG (kJ/mol) | m-value (kJ/mol/M) | $C_m$ (M) |
|---|---|---|---|
| C3 no DTT | 14.4 | 13.0 | 1.10 |
| C3 with DTT | 17.1 | 22.0 | 0.78 |
| C2V3 no DTT | 35.0 | 14.6 | 2.39 |
| C2V3 with DTT | 43.0 | 23.2 | 1.85 |

Free Cys residues effectively limit functional half-life due to reactive thioil chemistry (e.g. formation of thiol adducts) which contributes to an irreversible unfolding. Increases in functional half-life can be achieved by mutation to eliminate buried free Cys residues, even if such mutations decrease thermostability. However, increasing (or at least generally maintaining) thermostability is desirable also from a functional standpoint as increased stability can reduce proteolytic degradation, reduce aggregation, etc.

In human wild type FGF-1 there are 3 free Cys positions (17, 83, 117). With the exception of position 117, mutating these residues is destabilizing (and in the case of position 117 this is true except for mutation to Ala—which is essentially neutral). In some instances mutation of these residues results in a protein that is fractionally folded.

Rather than mutation, a solution to eliminating free thiols is to add another thiol and thereby create a disulfide bond with a free Cys residue in the protein. Mutation of Ala66 to Cys makes a disulfide with position Cys83. The combined mutation of C16S/A66C/C117V under oxidized conditions, where a disulfide is formed, has a midpoint of denaturation (1.10 M GuHCl) that is slightly destabilizing when compared to wild-type FGF-1 (1.23 M GuHCl—data not shown); thus, this mutation is destabilizing. However, the elimination of all free Cys residues likely creates pharmacological stability because the protein is less susceptible to degradation. The C2V3 mutant demonstrates that a modified FGF-1 protein is created that lacks reactive thiols and has improved thermostability.

Mass Spectrometry Analysis

C2 and C2V3 were mass spectrometry analysis. The oxidized protein samples were digested with trypsin overnight. The digested samples were split in half and one half of the sample was reduced with 10 mM DTT. The reduced and non-reduced protein digested samples were analyzed on AB Sciex 5800 MALDI-TOF/TOF tandem mass spectrometer. The data for C2 and C2V3 showed an addition of approximately 2 Da in the samples with DTT consistent with the addition of a hydrogen atom to each cysteine sulfur atom on disulfide bond reduction Differential Scanning Calorimetry (DSC)

C3 and C2V3 were analyzed on nanoDSC instrument in 50 mM Na phosphate, 100 mM NaCl with and without 2 mM TCEP. The concentration of each protein was about 0.5 mg/ml. Modified FGF-1 proteins tend to unfold irreversibly under heat and form protein aggregations. To analyze C3 and C2V3 on nanoDSC, different concentrations (0.4-1.2M) of GuHCl was incubated with each protein at 92° C. for 1 hour to determine the concentration of GuHCl protein at which aggregation of each protein was prevented. For C3, 0.7 M GuHCl was used when collecting the calorimetry data. For C2V3, 1.2 M GuHCl was used when collecting the calorimetry data.

NanoDSC scans of C3 in 50 mM Na phosphate, 100 mM NaCl, 0.7M GuHCl pH 7.5 were collected. The scans showed that this protein was too unstable to be analyzed using DSC. NanoDSC scans of C2V3 in 50 mM Na phosphate, 100 mM NaCl, 1.2M GuHCl, pH 7.5 were collected and analyzed by DSCfit software. NanoDSC scans of C2V3 in 50 mM Na phosphate, 100 mM NaCl, 1.2M GuHCl, pH 7.5 were collected analyzed by NanoAnalyze software. Results from the NanoAnalyze software were in good agreement with DSCfit software.

BaF3 Cell Proliferation Assay

Figure 2:
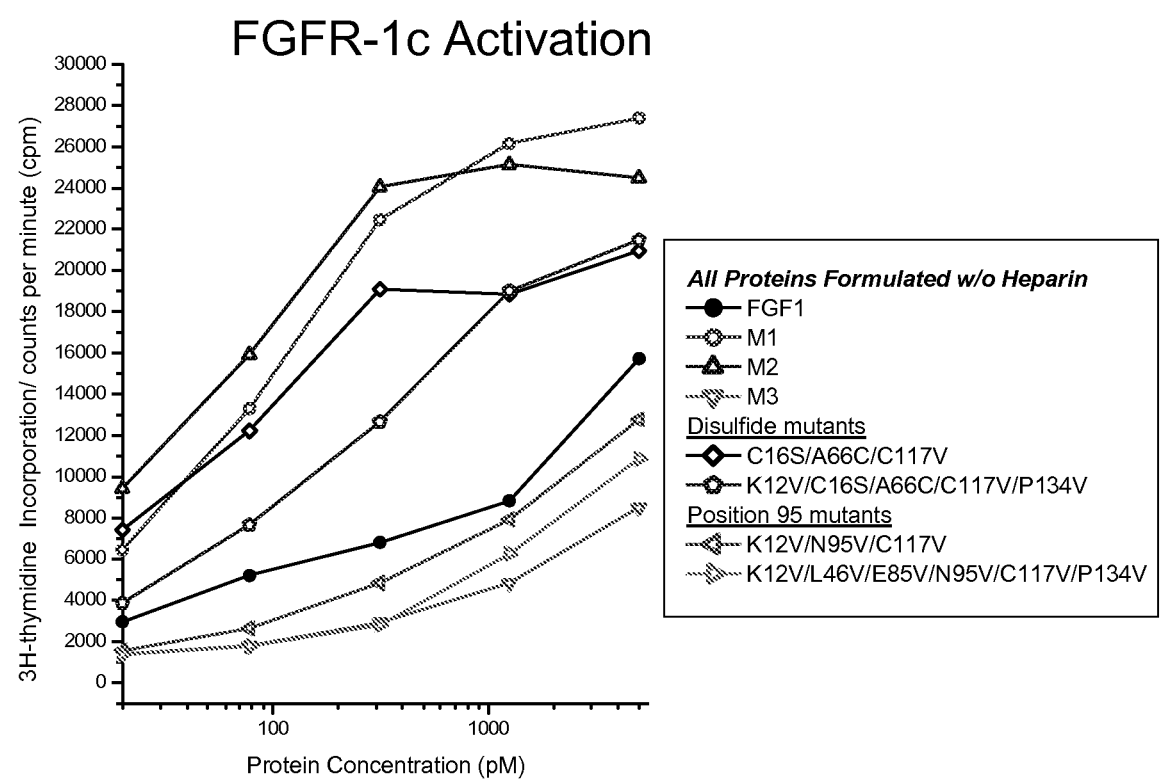
FIG. 2 depicts, as a non-limiting example, results from a BaF3 cell proliferation assay.
Figure 3:
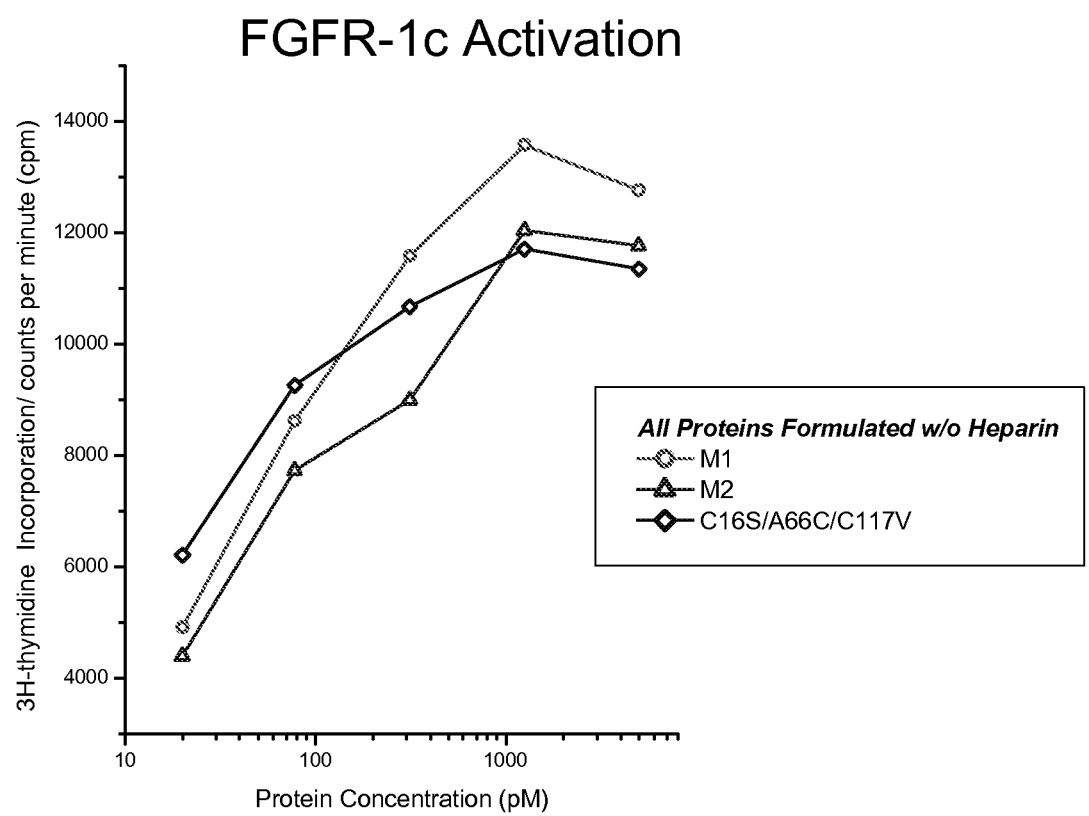
FIG. 3 depicts, as a non-limiting example, results from a BaF3 cell proliferation assay.

C3, C2V3, and M1 were tested for biological activity using a BaF3 cell proliferation assay. A low concentration of BaF3 cells expressing only FGFR1c isoform were seeded in 96 well plate including 1 µg/ml heparin. For each of C3, C2V3 and M1, a sample without heparin was diluted 4 times (concentration range 0-5 nM) with culture media with 1 µg/ml heparin and delivered to individual wells. Mitogenic activity was determined by adding 1 µCi of 3H-thymidine into each well. Cells were harvested after 4 hours incubation, and incorporated 3H-thymidine was counted on a scintillation counter. As a non-limiting example, results from a first BaF3 cell proliferation assay are depicted in FIG. 2. This figure illustrates, M1 (K12V/C117V/P134V), C3 (C16S/A66C/C117V), and C2V3 (K12V/C16S/A66C/C117V/P134V) each gave rise to a significant dose-responsive increase in 3H-thymidine incorporation indicating enhancement in cell proliferation. Thus, M1, C3, and C2V3 stimulated cell proliferation. As a non-limiting example, results from a second BaF3 cell proliferation assay are depicted in FIG. 3. This figure illustrates, M1 (K12V/C117V/P134V) and C3 (C16S/A66C/C117V) each gave rise to a significant dose-responsive increase in 3H-thymidine incorporation indicating enhancement in cell proliferation.

Example 5

Determination of Dose-Response Stimulation of CECs

FGF-1 is used as the base molecule for generation of modified FGFs because it is unique among FGFs in stimulating all seven FGF receptor isoforms. The FGF-1 proteins having the sequences of SEQ ID NO: 1, and eFGF-1, have been demonstrated to retain activity in a 3T3 cell proliferation assay (Dubey et al. *Journal of molecular biology*. 2007; 371(1):256-68.), and the amino acid substitutions and stabilization of the structure does result in any changes to the FGF receptor stimulation since there are minimal changes to the surface exposed residues.

Dose-response curves are determined for both migration (via the in vitro scratch assay) and mitogenic stimulation of CECs. Primary cultures of rabbit CECs are established using established procedures, e.g., the procedure described by Kay et al. (Kay et al. Investigative ophthalmology &visual science. 1993; 34(3):663-72; Lee et al., Investigative ophthalmology &visual science. 2009; 50(5):2067-76). Briefly, Descemet's membrane complex from rabbit eyes is treated with 0.2% collagenase and 0.05% hyaluronidase for 90 min at 37° C. Dissociated cells are cultured in DMEM supplemented with 15% fetal bovine serum and 50 µg/ml gentamycin. Cells are allowed to grow to confluence and are subculture using trypsin/EDTA. First passage cells are used for all experiments. The scratch assay is performed by allowing first passage cells to grow to confluence in 6-well plates and using a rubber policeman to create a scratch in the monolayer. Proliferation assays are performed in 12-well plates using, e.g., a Click-IT assay kit (Life Technologies). Dose response curves are generated for eFGF-1 in the presence and absence of heparin. FGF-1 (SEQ ID NO: 1) in the presence of heparin and FGF-2 are used as positive controls.

The doses proposed in the in vivo experiments are based on the assumption that the $ED_{50}$ for eFGF-1 is similar to the ED50 for the wild type FGF-1 (SEQ ID NO: 1). The determined $ED_{50}$ are used to adjust the dose for the in vivo experiments. The results indicate eFGF-1 stimulates migration and/or proliferation of the rabbit CECs.

Example 6

Demonstration that eFGF-1 Localizes to Areas of Corneal Injury or CEC Progenitors in Whole Cornea (Organ Culture) and In Vivo Via Anterior Chamber (Intracameral) Injection Effective therapy requires that the drug get to the target tissue and be present for long enough to act. Wild-type FGF-1 (wtFGF-1) requires a 3× mass excess of heparin for stability and the heparin in the formulation can interfere with the targeting of the FGF to the wound site in topical ophthalmic applications. Pharmacokinetic studies comparing wtFGF-1 with and without heparin to eFGF-1 confirm that the eFGF-1 partitions into the tissue compartment more effectively than wtFGF-1 and is released slowly from that compartment (Xia et al. *PloS one*. 2012; 7(11):e48210). Corneal injury activates stromal keratocytes to produce heparins (Brown et al., *Journal of cellular biochemistry*. 1995; 59(1):57-68).

The combination of the ability to administer eFGF-1 without heparin and the low protein concentration of the aqueous humor results in eFGF-1's localization to the endothelial surface and to exposed stroma in areas of lesion.

Labeled eFGF-1 is used to demonstrate eFGF-1 is bound to the tissue compartment and releases slowly, first in whole organ cultured corneas and then in vivo following intracameral administration.

eFGF-1 is labeled with dye as described in the art (Xu, et al., *The Journal of biological chemistry*. 2012; 287(47): 40061-73). Briefly, in this procedure the eFGF-1 is complexed with heparin before dye derivatization so that the dye is not bound to the heparin binding site and therefore derivatization does not disrupt heparin binding. It is still possible that the dye may bind to receptor binding areas of the protein, but the initial interactions with tissue are predominantly via proteoglycans rather than the FGF receptors, and the amount of eFGF-1 bound to receptors is not detectable in this assay.

To model intracameral injection of eFGF-1 using corneal organ culture, explanted corneas including the peripheral cornea are incubated in labeled eFGF for 30 minutes followed by rinsing for varying periods of time in media without labeled FGF. Corneas are scratched to create an endothelial lesion across the central cornea. Corneas are used immediately or are incubated in culture media for 24 hours after scratching to allow expression of heparans by the stromal cells before assaying eFGF-1 binding. To evaluate the dependence of binding on heparins, corneas are exposed to labeled eFGF-1 in the absence or presence of heparin (10 ug/ml).

Example 7

Acceleration of Corneal Healing in an In Vivo Animal Model

This study is directed to semi-quantitative in vivo PK measurements. For in vivo experiments, labeled eFGF-1 is administered by intracameral injection via the peripheral cornea in the absence of heparin, and the fluorescently labeled protein followed by periodic inspection via confocal fluorescence microscopy with Heidelberg Retinal Tomography (HRT)+Rostock Cornea Module. Injected eyes are evaluated at 30 min, 2 hours, 8 hours, 24 hours and 48 hours post injection. If label is still present at 48 hours, animals are followed for up to 2 weeks.

The administration paradigm in the in vivo experiment assumes that the binding of the eFGF-1 to the cornea can be measured and that the time course of disappearance of the bound eFGF-1 is at least as long as that expected by dilution of the aqueous ($t_{1/2}$ of about 90 minutes). In the event that the disappearance of the eFGF-1 follows a more rapid course, eFGF-1 is administered more frequently in the animal model.

Once eFGF-1 is confirmed to stimulate the CECs and an $EC_{50}$ established, the effect of eFGF-1 in vivo is measured using the rabbit transcorneal freeze damage model of corneal endothelial damage (Okumura et al. *The British journal of ophthalmology.* 2011; 95(7):1006-9). Briefly, a 7 mm steel probe is frozen in liquid nitrogen and then held to the cornea of the rabbit for 15 s. This freezes the cornea through to the endothelial cell layer and generates a reproducible region of CEC loss, with corneal edema and a cell free area of the inner corneal surface 24 hours later.

Rabbits are subjected to transcorneal freezing under general anesthesia. The contralateral eye serves as a control. Once the ice ball in the anterior chamber has melted, the lesions are imaged microscopically and photographed to verify appropriate lesion generation and size. eFGF-1 is administered intracamerally via a 30 ga needle into the aqueous via the peripheral cornea. Injection occurs across an area of cornea distant from the lesion. Corneas are examined microscopically and photographed at 24 and 48 hrs, including OCT imaging of corneal thickness to evaluate damage to the stroma as well as confocal microscopy with the HRT and CEC counting. At 48 hours, the animals are sacrificed and corneas are harvested and are stained with alizarin red. The area of the endothelial lesions are quantitated using image analysis.

eFGF is administered intracamerally starting at a dose of 100 ng (10 ul of a 10 ug/ml solution) in saline approximately 60 min after lesioning. A 100 ng dose into the aqueous of a rabbit gives an initial concentration of approximately 400 ng/ml and given the turnover of aqueous humor of 2-3 ul/min the concentration of eFGF-1 in the aqueous falls below 2 ng/ml (the $ED_{50}$ in the 3T3 cell assay (Dubey et al. *Journal of molecular biology.* 2007; 371(1):256-68)) at 11 hours post dose. On this basis, only a single dose of the eFGF-1 is administered for these experiments, and the dosing frequency is adjusted if no effect is seen at this dose. Agonists such as FGF-1 often exhibit a bell shaped dose response curve; therefore, other groups of animals are treated with lower or higher doses to establish a dose response curve.

In the rabbit model, administration of the Rho kinase (ROCK) inhibitor Y-27632 reduces the area of lesion to 20% of control at 48 hours post lesion. In in vitro models, FGF-2 alone produces a larger effect on migration of endothelial cells than Y-27632 and the two are synergistic (Lee et al. *Investigative ophthalmology & visual science.* 2006; 47(4): 1376-86). If eFGF-1 produces an effect at least similar in size to the ROCK inhibitor, six animals per dose group provides a statistically significant result.

These experiments demonstrate that eFGF-1 is a potential treatment for FD and other endothelial dystrophies and lays the groundwork for phase II, in which these experiments are repeated with human corneal endothelial cells in vitro and primates in vivo. This efficacy data is sufficient to support an IND filing for the use of eFGF-1 in patients that have dystrophy sufficient to be considered for corneal transplants.

Example 8

Use of a Modified FGF in Patients Undergoing Photorefractive Keratotomy (PRK)

Patients who have undergone PRK are treated with a suitable ophthalmic formulation (e.g., a topical solution of 1 mg/ml (0.1%) eFGF-1 as an eye drop formulated in phosphate buffered saline). The eye drop is administered daily, e.g., three to four times a day for 7 days. These treated patients experience reepithelialization of the cornea more quickly than untreated patients. Reepithelialization of the cornea is observed fluorescein or lissamine green staining as well as biomicroscopy.

Example 9

Use of a Modified FGF in Patients with Corneal Endothelial Dystrophy

Patients who have corneal endothelial dystrophy (e.g., Fuch's dystrophy) are treated with a suitable ophthalmic formulation (e.g., a solution of 1 mg/ml (0.1%) eFGF-1 formulated in phosphate buffered saline). The FGF solution is administered via intracameral injection every 1-3 months. These treated patients experience increase in the density of the endothelial cells in the central cornea more quickly than untreated patients. The increase in corneal endothelial cell density is viewed using specular microscopy.

Example 10

Use of Modified FGF in Patients Undergoing Trabeculectomy

Patients undergoing trabeculectomy are treated with a modified FGF (e.g. a modified FGF-1 having the sequence of SEQ ID NO: 2, a modified FGF-1 having the sequence of SEQ ID NO: 3, or a modified FGF-1 having the sequence of SEQ ID NO: 4) in a suitable ophthalmic formulation (e.g., a solution of 1 mg/ml (0.1%) of a modified FGF-1 (e.g. a modified FGF-1 having the sequence of SEQ ID NO: 2, a modified FGF-1 having the sequence of SEQ ID NO: 3, or a modified FGF-1 having the sequence of SEQ ID NO: 4) formulated in phosphate buffered saline or as a sustained release formulation applied to the trabeculectomy site). These patients experience more rapid healing of the trabeculectomy site with reduced fibrosis and reduced fibrotic obstruction of the trabeculectomy canal.

What is claimed is:

1. A method of ameliorating Fuch's dystrophy, comprising administering to a mammal in need thereof, a pharmaceutical composition comprising: (i) a modified FGF-1 comprising the sequence of SEQ ID NO: 3, and (ii) a pharmaceutically acceptable carrier, excipient, or diluent,
    wherein the Fuch's dystrophy is characterized by an epithelial-mesenchymal transition of corneal endothelial cells of the mammal, and wherein the administering the pharmaceutical composition results in reversal of the epithelial-mesenchymal transition of corneal endothelial cells.

2. The method of claim 1, wherein the pharmaceutical composition is a liquid ophthalmic formulation.

3. The method of claim 1, wherein the pharmaceutical formulation is administered topically, by microneedle into the cornea, or intracamerally.

4. The method of claim 1, wherein the pharmaceutical composition comprising the modified FGF-1 does not comprise heparin.

5. The method of claim 1, wherein the mammal is a human.

* * * * *